(12) United States Patent
Reasoner et al.

(10) Patent No.: US 11,446,423 B2
(45) Date of Patent: Sep. 20, 2022

(54) AUTONOMOUS WASTE COLLECTION ASSEMBLY AND MEDICAL WASTE COLLECTION SYSTEM AND METHODS

(71) Applicant: Stryker Corporation, Kalamazoo, MI (US)

(72) Inventors: Stephen J. Reasoner, Kalamazoo, MI (US); Andy Staats, Issaquah, WA (US); Brian MacLachlan, Norton Shores, MI (US); Tamitha M. Dollman, Hampton, AL (US)

(73) Assignee: Stryker Corporation, Kalamazoo, MI (US)

( * ) Notice: Subject to any disclaimer, the term of this patent is extended or adjusted under 35 U.S.C. 154(b) by 341 days.

(21) Appl. No.: 16/755,215

(22) PCT Filed: Oct. 23, 2018

(86) PCT No.: PCT/US2018/057088
§ 371 (c)(1),
(2) Date: Apr. 10, 2020

(87) PCT Pub. No.: WO2019/083992
PCT Pub. Date: May 2, 2019

(65) Prior Publication Data
US 2020/0254154 A1  Aug. 13, 2020

Related U.S. Application Data

(60) Provisional application No. 62/575,833, filed on Oct. 23, 2017.

(51) Int. Cl.
*B60L 53/36*   (2019.01)
*A61M 1/00*   (2006.01)
(Continued)

(52) U.S. Cl.
CPC ............... *A61M 1/63* (2021.05); *B60L 53/36* (2019.02); *G05D 1/0088* (2013.01);
(Continued)

(58) Field of Classification Search
CPC ............ A61M 1/63; A61M 2205/3389; A61M 2205/502; A61M 2205/52;
(Continued)

(56) References Cited

U.S. PATENT DOCUMENTS 6,046,565 A    4/2000  Thorne
7,066,291 B2   6/2006  Martins et al.
(Continued)

FOREIGN PATENT DOCUMENTS

CA    2625885 A1    4/2007
CA    2625895 A1    4/2007
(Continued)

OTHER PUBLICATIONS

Abate, Carolyn, "Is Da Vinci Robotic Surgery a Revoluation or a Rip-Off?", Healthline, http://www.healthline.com/health-news/is-da-vinci-robotic-surgery-revolution-or-ripoff-021215, 2016, 25 pages.
(Continued)

*Primary Examiner* — Mary Cheung
(74) *Attorney, Agent, or Firm* — Howard & Howard Attorneys PLLC

(57) ABSTRACT

An autonomous medical waste collection assembly comprises a base adapted to be positioned near a patient. At least one wheel is powered to move the base along a floor surface. A waste collection unit is coupled to the base for receiving medical waste from the patient. The waste collection unit includes a canister for holding the medical waste. A controller is operable to initiate a waste disposal protocol. The waste disposal protocol includes transmitting a movement signal to the powered wheel for automatically moving the
(Continued)

autonomous medical waste collection assembly away from the patient to a disposal station. A user input device is in communication with the controller. The user input device is adapted to provide a user input signal in response to being actuated by a user. The controller is configured to initiate the waste disposal protocol in response to receiving the user input signal.

21 Claims, 10 Drawing Sheets

(51) Int. Cl.
G05D 1/00 (2006.01)
G05D 1/02 (2020.01)
(52) U.S. Cl.
CPC .............. *A61M 2205/3389* (2013.01); *A61M 2205/502* (2013.01); *A61M 2205/52* (2013.01); *A61M 2209/01* (2013.01); *A61M 2209/086* (2013.01); *G05D 1/0225* (2013.01); *G05D 2201/0206* (2013.01)
(58) Field of Classification Search
CPC ........ A61M 2209/01; A61M 2209/086; A61M 2205/10; A61M 2205/3561; A61M 2205/3576; A61M 2205/8262; A61M 2209/084; B60L 53/36; G05D 1/0088; G05D 1/0225; G05D 2201/0206; G05D 1/0234; Y02T 10/70; Y02T 10/7072; Y02T 90/12; Y02T 90/16
See application file for complete search history.

(56) References Cited

U.S. PATENT DOCUMENTS

| | | | |
|---|---|---|---|
| 7,100,725 | B2 | 9/2006 | Thorne |
| 7,431,115 | B2 | 10/2008 | Thorne |
| 7,615,037 | B2 | 11/2009 | Murray et al. |
| 7,621,828 | B2 | 11/2009 | Voges et al. |
| 7,621,898 | B2 | 11/2009 | Lalomia et al. |
| 7,894,939 | B2 | 2/2011 | Zini et al. |
| 7,996,109 | B2 | 8/2011 | Zini et al. |
| 8,010,230 | B2 | 8/2011 | Zini et al. |
| 8,041,455 | B2 | 10/2011 | Thorne |
| 8,204,624 | B2 | 6/2012 | Zini et al. |
| 8,216,199 | B2 | 7/2012 | Murray et al. |
| 8,740,866 | B2 | 6/2014 | Reasoner et al. |
| 8,789,638 | B2 | 7/2014 | Zhang et al. |
| 8,886,390 | B2 | 11/2014 | Wolfe et al. |
| 8,915,897 | B2 | 12/2014 | Murray et al. |
| 8,948,914 | B2 | 2/2015 | Zini et al. |
| 8,955,870 | B2 | 2/2015 | Lee et al. |
| 9,020,679 | B2 | 4/2015 | Zini et al. |
| 9,026,301 | B2 | 5/2015 | Zini et al. |
| 9,052,718 | B2 | 6/2015 | Hyde et al. |
| 9,223,313 | B2 | 12/2015 | Wolfe et al. |
| 9,233,039 | B2 | 1/2016 | Hyde et al. |
| 9,245,305 | B2 | 1/2016 | Wellington et al. |
| 9,436,926 | B2 | 9/2016 | Cousins et al. |
| 9,465,389 | B2 | 10/2016 | Hyde et al. |
| 9,535,421 | B1 | 1/2017 | Canoso et al. |
| 9,563,205 | B2 | 2/2017 | Binney et al. |
| 9,563,206 | B2 | 2/2017 | Zini et al. |
| 9,579,428 | B1 | 2/2017 | Reasoner et al. |
| 9,592,969 | B2 | 3/2017 | Wolfe et al. |
| 9,618,931 | B2 | 4/2017 | Zini et al. |
| 9,619,617 | B2 | 4/2017 | Skirble et al. |
| 9,821,965 | B2 | 11/2017 | Wolfe et al. |
| 2007/0135779 | A1* | 6/2007 | Lalomia .............. A61M 1/0023 604/319 |
| 2015/0227885 | A1 | 8/2015 | Zini et al. |
| 2016/0070267 | A1 | 3/2016 | Hyde et al. |
| 2016/0110684 | A1 | 4/2016 | Wellington et al. |
| 2016/0364686 | A1 | 12/2016 | Wolfe et al. |

FOREIGN PATENT DOCUMENTS

| | | | | |
|---|---|---|---|---|
| CA | 2837477 | A1 | 4/2007 | |
| CA | 2864027 | A1 | 4/2007 | |
| CA | 2849739 | A1 | 3/2013 | |
| CN | 201729172 | U | 2/2011 | |
| CN | 103817123 | A * | 5/2014 | ........... B08B 9/0821 |
| CN | 105701361 | A | 6/2016 | |
| DK | 1587725 | T3 | 3/2014 | |
| HK | 1199121 | A1 | 6/2015 | |
| JP | 5807990 | B2 | 11/2015 | |
| RU | 2392541 | C1 * | 6/2010 | |
| WO | 2004020267 | A2 | 3/2004 | |
| WO | 2013044069 | A1 | 3/2013 | |
| WO | 2013059423 | A1 | 4/2013 | |
| WO | 2015120473 | A1 | 8/2015 | |
| WO | 2016205318 | A1 | 12/2016 | |

OTHER PUBLICATIONS

Atheon, "Atheon TUG Webpage", 2017, https://aethon.com/products/, 4 pages.
Bad Robot Surgery, "Bad Robot Surgery Facebook Page", https://www.facebook.com/BadRobotSurgery/?ref=page_internal, 2012, 1 page.
Caddytrek, Caddytrek Webpage, 2017, https://www.caddytrek.com/, 7 pages.
International Search Report for Application No. PCT/US2018/057088 dated Feb. 5, 2019, 3 pages.
IRobot, "iRobot Reviews", Consumer Affairs, 2017 (updated 2020), https://www.consumeraffairs.com/homeowners/irobot.html, 9 pages.
Joelving, Frederik, "Pricey Surgery Robots Lack Clear Benefits: Study", Reuters, http://www.reuters.com/article/us-pricey-robots-idUSTRE80T1SC20120130, Jan. 30, 2012, 10 pages.
Murphy, Mike, "Robots are Now Fighting Fires in Australia", Quartz, Dec. 11, 2015, https://qz.com/571881/robots-are-now-fighting-fires-in-australia/, 4 pages.
Murphy, Mike, "These are the Robots Competing to One Day Save Your Life", Quartz, Jun. 4, 2015, https://qz.com/420056/these-are-the-robots-competing-to-one-day-save-your-life/, 11 pages.
Palermo, Elizabeth, "Fire Fighting Robots Could Help US Navy Snuff Out Fires at Sea", LiveScience, Feb. 5, 2015, http://www.livescience.com/49719-humanoid-robot-fights-fires.html, 5 pages.
Plackett, Benjamin, "Rescue Me, Robot—Machines Ready for Firefighting Duty", Wired, Mar. 18, 2012, https://www.wired.com/2012/10/fire-fighting-robots/, 9 pages.
Wikipedia, "Atlas (Robot)", 2015, https://en.wikipedia.org/wiki/Atlas_%28robot%29, 4 pages.
Youtube, "How the Tesla Model S is Made—Tesla Motors Part 1 (Wired)", Jul. 16, 2013, https://youtu.be/8_IfxPI5ObM, 3 pages.
Youtube, "A Day in the Life of a Kiva Robot", May 11, 2011, https://youtu.be/6KRjuuEVEZs, 2 pages.
Youtube, "Amazon Warehouse Robots: Mind Blowing Video", Jul. 26, 2016, https://youtu.be/cLVCGEmkJs0, 2 pages.
Youtube, "Electric Car Quality Tests—Tesla Motors Part 3 (Wired)", Aug. 13, 2013, https://youtu.be/YVqIZO7tHFE, 2 pages.
Youtube, "High Speed Robots Part 1: Meet BettyBot in 'Human Exclusion Zone' Warehouses—The Window—Wired", Jul. 2, 2013, https://youtu.be/8gy5tYVR-28, 2 pages.
Youtube, "High Speed Robots Part 2: Kiva Robots in the Workplace and in Our E-Commerce Economy—The Window_Wired", Jul. 2, 2013, https://www.youtube.com/watch?v=qU4YMDJNzpg&feature=youtu.be, 2 pages.
Youtube, "How Tesla Builds Electric Cars—Tesla Motors Part 2 (Wired)", Jul. 30, 2013, https://youtu.be/TEReFPI4jSc, 2 pages.
Youtube, "How Tesla's Self-Driving Auto Pilot Actualy Works", Aug. 17, 2016, https://youtu.be/AiOxUcDgsa8, 2 pages.
Youtube, "Meet Amazon's New Robot Army Shipping Out Your Products", Dec. 2, 2014, https://youtu.be/g6DIFpaoI6A, 2 pages.

(56) References Cited

OTHER PUBLICATIONS

Youtube, "Nick's Tesla—My Drive to Work Using Autopilot", Jan. 30, 2017, https://youtu.be/aTvzsJUtkVo, 2 pages.
Youtube, "Trying to Kill My Friend, Tesla Autopilot Saves Him!", Nov. 16, 2016, https://youtu.be/xkDOX8mZp3Y, 2 pages.
English language abstract and machine-assisted english translation for CN 201729172 extracted from espacenet.com database on May 14, 2020, 5 pages.
English language abstract for CN 105701361 extracted from espacenet.com database on May 14, 2020, 2 pages.
English language abstract for HK 1199121 extracted from espacenet.com database on May 14, 2020, 2 pages.
English language abstract for JP 5807990 extracted from espacenet.com database on May 14, 2020, 2 pages.

* cited by examiner

AUTONOMOUS WASTE COLLECTION ASSEMBLY AND MEDICAL WASTE COLLECTION SYSTEM AND METHODS

CROSS REFERENCE TO RELATED APPLICATIONS

This is a United States national stage entry of International Patent Application No. PCT/US2018/057088, filed on Oct. 23, 2018, which claims priority to and all the benefits of U.S. Provisional Patent Application No. 62/575,833, filed Oct. 23, 2017, the entire contents of each are hereby incorporated by reference.

BACKGROUND

Medical waste collection devices may be used in a hospital or other health care setting. For example, mobile rovers are employed to collect medical waste such as bodily fluids, body tissues, irrigation liquids, and smoke during medical and surgical procedures. The medical waste is often stored in a canister mounted to the medical waste collection device that must be emptied and cleaned before, during, or after the procedures. Currently, hospital personnel such as nurses and operating room assistants must suspend their duties to carry or wheel the medical waste collection devices or canisters thereof to disposal stations to empty and clean the canisters. This requires the hospital personnel to move a medical waste collection device to a disposal station, wait for an emptying and cleaning procedure to be performed, move the medical waste collection device back to the operating room, reenter the operating room, and set up the medical waste collection device again before surgery can be commenced or resumed. Furthermore, the medical waste collection devices can require battery power and therefore must be charged before, during or after the procedure, thereby requiring even more time and effort of the hospital personnel. Therefore, there is a need for a waste collection device and system that overcomes one or more of the aforementioned disadvantages.

SUMMARY

An autonomous medical waste collection assembly autonomously collects and disposes of medical waste generated during medical procedures (e.g., surgical procedures) performed in a health care facility such as a hospital. The medical waste may include bodily fluids, body tissues, irrigation liquids, and/or other materials that may be generated during various medical procedures. During the medical procedure, the assembly collects the medical waste and stores the medical waste on-board until such a time as a user is ready to have the assembly autonomously off-load the medical waste and dispose of the medical waste. Once the medical waste fills the assembly or the user is ready to dispose of the medical waste, the assembly autonomously navigates to a docking station. At the docking station, the medical waste is emptied from the assembly to a drain or treatment area and the assembly is cleaned for further use.

According to one exemplary embodiment of the present disclosure, the autonomous medical waste collection assembly comprises a base adapted to be positioned near a patient. Wheels are coupled to the base. At least one of the wheels is powered to move the base along a floor surface. A waste collection unit is coupled to the base for receiving medical waste from the patient. The waste collection unit includes a canister and a suction pump. The canister is for holding the medical waste. The suction pump is in fluid communication with the canister and configured to draw a suction on the canister. A controller is operable to initiate a waste disposal protocol. The waste disposal protocol includes transmitting a movement signal to the powered wheel for automatically moving the autonomous medical waste collection assembly away from the patient to a disposal station. A user input device is in communication with the controller. The user input device is adapted to provide a user input signal in response to being actuated by a user. The controller is configured to initiate the waste disposal protocol in response to receiving the user input signal.

In another exemplary embodiment, a medical waste collection system is provided. The system comprises a disposal station, and an autonomous medical waste collection assembly. The disposal station includes a housing and a coupler. The coupler is coupled to the housing. The autonomous medical waste collection assembly includes a base, wheels, a waste collection unit, a counterposing coupler, and a controller. The base is adapted to be positioned near a patient. The wheels are coupled to the base. At least one of the wheels is powered to move the base along a floor surface. The waste collection unit is coupled to the base for receiving medical waste from the patient. The waste collection unit includes a canister and a suction pump. The canister is for holding the medical waste. The suction pump is in fluid communication with the canister and configured to draw a suction on the canister. The counterposing coupler is coupled to the base. The counterposing coupler is adapted to be removably coupled with the coupler of the disposal station. The controller is operable to initiate a waste disposal protocol. The waste disposal protocol includes transmitting a movement signal to the powered wheel for automatically moving the autonomous medical waste collection assembly away from the patient to the disposal station such that the coupler couples with the counterposing coupler to provide a connection between the autonomous medical waste collection assembly and the disposal station.

BRIEF DESCRIPTION OF THE DRAWINGS

Advantages of the present invention will be readily appreciated, as the same becomes better understood by reference to the following detailed description, when considered in connection with the accompanying drawings.

DETAILED DESCRIPTION

Figure 1:
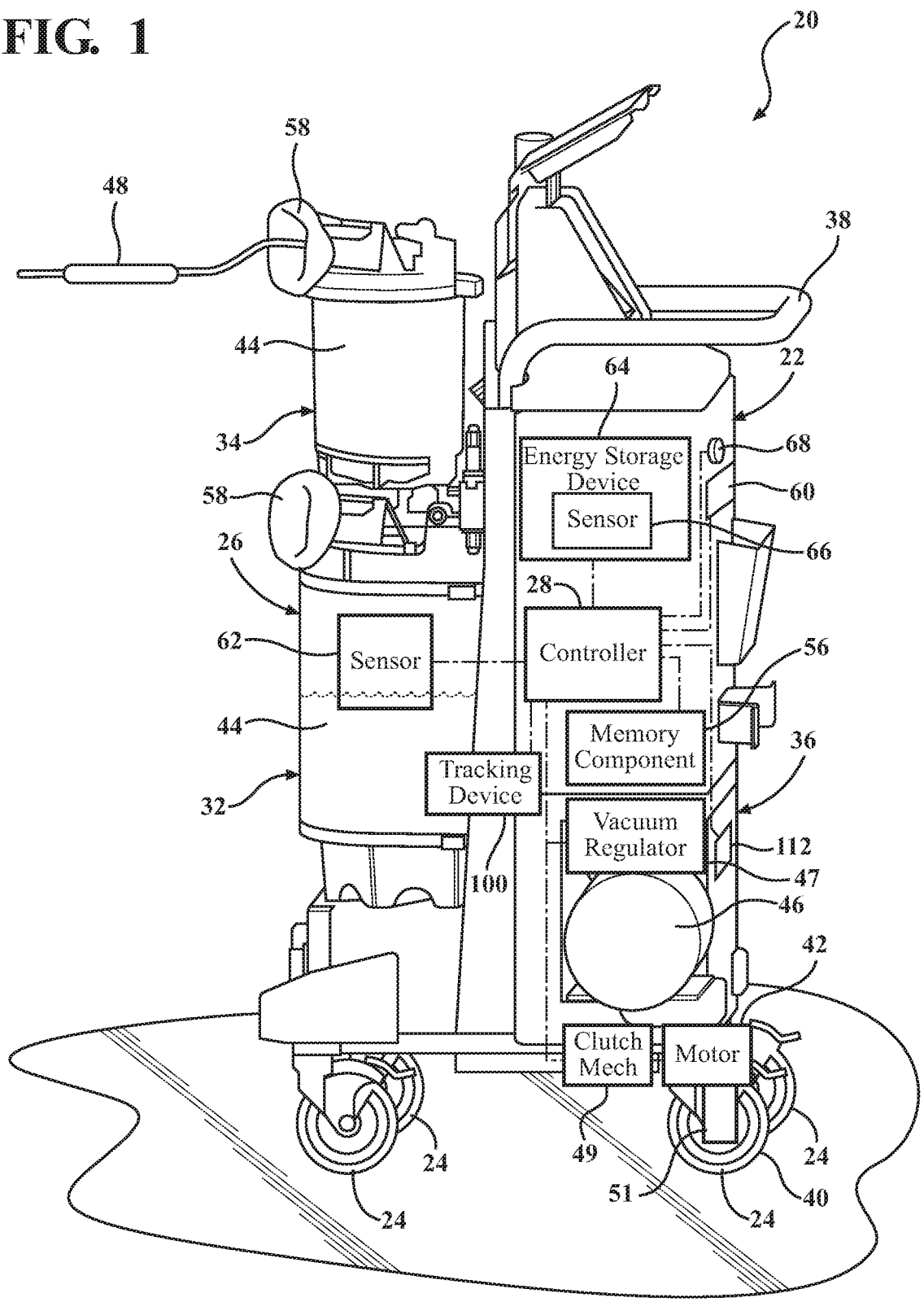
FIG. 1 is a perspective view of an embodiment of an autonomous medical waste collection assembly with schematic representations of select electrical componentry.

Referring to the Figures, wherein like numerals indicate like or corresponding parts throughout several views, aspects of an autonomous medical waste collection assembly 20 are provided. The assembly 20 may include a base 22, a plurality of wheels 24, a waste collection unit 26, and a controller 28. The base 22 is adapted to be positioned near a patient 30 during the medical procedure. The base 22 supports the waste collection unit 26. FIG. 1 shows an embodiment of the assembly 20 where the base 22 includes a lower frame 32, an upper frame 34, a vertical chassis 36, and a handle 38. The base 22 can have any suitable shape.

The plurality of wheels 24 is coupled to the base 22 to provide mobility to the assembly 20. For example, the assembly 20 can autonomously move around a health care facility to collect the medical waste generated during medical procedures performed in different locations throughout the health care facility. The wheels can be coupled to the lower frame 32, the vertical chassis 36, or a combination thereof. FIG. 1 shows an embodiment wherein two of the wheels 24 are coupled to the lower frame 32, and another two of the wheels 24 are coupled to the vertical chassis 36. In some embodiments, one or more of the plurality of wheels 24 is a steerable wheel, such as a wheel capable of swiveling on an axis. In still other embodiments, the plurality of wheels 24 includes a combination of one or more fixed wheels and one or more steerable wheels. At least one of the wheels 24 is a powered wheel 40 to facilitate autonomous movement of the assembly 20. FIG. 1 shows an embodiment of the assembly 20 having four wheels 24, one of which is powered. The powered wheel 40 is powered by a motor 42 such that the powered wheel 40 can move the assembly 20 along a floor surface of the health care facility. The motor 42 can be a brushed electric motor, a brushless electric motor, a stepper motor, a servomotor, an alternating current motor, or any other suitable type of motor for powering the powered wheel 40 to move the assembly 20. The motor 42 is in communication with the controller 28. The controller 28 can drive, steer, and/or navigate the assembly 20 through the medical facility by selectively powering and/or steering the powered wheel 40. For example, in some embodiments the controller 28 is configured to drive, steer, and navigate the assembly 20 by selectively swiveling and powering the powered wheel 40. In some embodiments, several of the wheels 24 are powered wheels 40, and each of the powered wheels 40 has the motor 42 attached thereto. Each of the motors is connected to the controller 28. The controller 28 can drive, steer, and navigate the assembly 20 by selectively swiveling and powering the powered wheels 40. In embodiments where the powered wheels 40 are fixed wheels, the controller 28 is configured to steer the assembly 20 by selectively powering the powered wheels 40, such as by driving one of the powered wheels 40 in an opposite rotational direction of other of the powered wheels 40, thereby turning the assembly 20.

The controller 28 is configured to execute computer-executable instructions to perform the functions of the assembly 20, such as initiating the waste disposal protocol or the charging protocol. The controller 28 may be a microprocessor, a microcontroller, a field programmable gate array (FPGA), a system on a chip (SoC), or any other suitable type of controller for executing the functions of the assembly 20.

The assembly 20 includes a memory component 56 in communication with the controller 28. The memory component 56 is configured to store computer-executable instructions to be executed by the controller 28. The memory component 56 stores computer-executable instructions defining the waste disposal protocol and/or the charging protocol. The memory component 56 may include random access memory (RAM), flash memory, non-volatile random access memory (NOVRAM), and/or any other suitable form of memory.

The waste collection unit 26 is coupled to the base 22 and configured to receive medical waste from the patient during the medical procedure. The assembly 20 collects the medical waste by suction during the medical procedure and stores the medical waste in the waste collection unit 26. In some embodiments, the assembly 20 also collects smoke, such as smoke generated during electrocautery procedures. In other embodiments, the assembly 20 is configured to filter particles from the smoke and release filtered air. The waste collection unit 26 includes at least one canister 44 configured to hold the medical waste, a suction pump 46, and a vacuum regulator 47. In the illustrated embodiment shown in FIG. 1, the assembly 20 includes two canisters 44. The canisters 44 can be coupled to the lower frame 32, the upper frame 34, or a combination thereof. FIG. 1 shows an embodiment wherein a first canister is coupled to the upper frame 34 and a second canister is coupled to the lower frame 32. The canister(s) 44 can be substantially cylindrical, frustoconical in shape, or any suitable shape for containing the medical waste. The canister 44 can be formed of glass or suitable plastic material, or a combination thereof. The suction pump 46 is in fluid communication with the canister 44. In some embodiments, as shown in FIG. 1, the suction pump 46 is coupled to the vertical chassis 36. The suction pump 46 is configured to draw a suction on the canister 44 to draw the medical waste, such as liquid medical waste, into the canister 44 during the medical procedure. In some embodiments, the suction pump 46 is a rotary vane type vacuum pump mounted to the base 22. The vacuum regulator 47 is in communication with the suction pump 46 and configured to regulate a level of the vacuum drawn through the suction line. An exemplary vacuum regulator 47 arrangement suitable for the assembly 20 is disclosed in commonly owned U.S. Pat. No. 7,621,898 issued Nov. 29, 2009, the entire contents of which are hereby incorporated by reference.

During a surgical procedure, a user such as a surgeon, nurse, or operating room assistant holds an end of a suction line 48, such as a flexible tube, near or on a portion of the patient 30 where medical waste is present. The suction pump 46 provides suction to move the medical waste from the end of the suction line 48 through the suction line 48 and into the waste collection unit 26. During some procedures, the end of the suction line 48 is connected to an end effector such as an endoscope, an electrocautery tool, an ablation device, or any other type of surgical end effector or surgical tool. The suction pump 46 provides suction to move the medical waste through both the end effector and the suction line 48 and into the waste collection unit 26. The level of suction is regulated by the vacuum regulator 47, and/or a level of power supplied to the suction pump 46. For example, during a bone ablation procedure, medical waste is generated in the form of bodily fluids such as blood, tissues such as skin tissue, muscle tissue, and connective tissue, and particles of bone released during ablation. Furthermore, an area of the body of the patient where the procedure is being performed is often irrigated with saline to flush the bodily fluids, tissues, and particles from the area being ablated. The medical waste also includes the saline. The surgeon can use an ablation tool to ablate the bone, and the end of the tool can be coupled to the ablation tool. As the ablation tool ablates the bone, the medical waste can be suctioned through the suction line 48 coupled to the ablation suction line 48 and into the canister 44 of the waste collection unit 26 for disposal during or after completion of the ablation procedure.

The assembly 20 may include a manifold receiver 58 coupled to the canister 44 and an indicator 60 coupled to the base 22 and in communication with the controller 28. The manifold receiver 58 is configured to receive a disposable manifold (not shown), such as described in commonly owned U.S. Pat. No. 7,615,037, issued Nov. 10, 2009, the entire contents of which is hereby incorporated by reference. The disposable manifold directs the medical waste from the patient 30 through the suction line 48 and into the canister 44 during the medical procedure. The disposable manifold is disposed of between medical procedures, between use with different patients, and/or before disposal of the medical waste at the disposal station 50. In some embodiments, the indicator 60 is configured to alert the user to remove and dispose of the disposable manifold prior to initiation of a disposal protocol to be described. The indicator 60 is also configured to alert the user regarding other alerts to be described. The indicator 60 can be, for example, an LED, a video screen, a label, or any visual indicia, tactile indicia, auditory alert or other suitable type of indicator.

The assembly 20 includes a waste sensor 62 in communication with the controller 28. The waste sensor 62 is configured to sense an amount of the medical waste contained within the canister 44. The waste sensor 62 can be, for example, a sensor rod configured to run through the canister 44 with a plurality of reflecting elements and float elements situated nearby to facilitate sensing the amount of the medical waste. In embodiments where the assembly 20 includes a plurality of canisters 44, amounts of the medical waste contained in each of the canisters 44 can be measured by a separate waste sensor 62. The waste sensor 62 can include a waste sensor controller (not shown) configured to facilitate sensing of the amount of the medical waste. In some embodiments, the waste sensor 62 is configured to provide a waste level signal to the controller 28 when the amount of the medical waste sensed by the waste sensor 62 exceeds a waste threshold level. In other embodiments, the waste sensor 62 is configured to regularly or continuously provide the waste level signal to the controller 28. The indicator 60 can display indicia corresponding to the waste level signal such that the user can learn the amount of the medical waste sensed by the waste sensor 62 by looking at the indicator 60. The waste threshold level can be a level of medical waste contained in the canister 44 that is indicative of the canister 44 being full or nearly full and therefore necessitating disposal of the medical waste contained in the canister 44 before more of the medical waste is collected. In some embodiments, the waste threshold level is stored in the memory component 58 in communication with the controller 28. The waste threshold level can be configured relative to a total volume of the canister 44 suitable for containing the medical waste, e.g., 100% of the volume of the canister 44 or 80% of the volume of the canister 44. Conversely, the waste threshold level can be configured to a volume of the medical waste, e.g., 1.5 liters of the medical waste or 0.8 liters of the medical waste. Additionally, the waste threshold level can be a preset threshold level configured during manufacture and/or programming of the assembly 20. The waste threshold level can otherwise, or additionally, be a threshold level configurable by hospital personnel or the user before, during, or after the medical procedure. In some embodiments, the waste threshold level is configurable depending on the nature of the medical waste. Some medical procedures generate more hazardous or toxic medical waste relative to other medical procedures, such as large amounts of hazardous blood and tissue being collected or large amounts of non-hazardous saline fluid being collected during the medical procedure. When the assembly 20 is used to collect the medical waste during procedures for which the medical waste is relatively non-hazardous or non-toxic, the waste threshold level may be set to a higher volume or set higher relative the volume of the canister 44 in order to maximize efficiency of the waste collection. When the assembly 20 is used to collect the medical waste during procedures for which the medical waste is relatively hazardous or toxic, the waste threshold level may be set to a lower volume or lower relative the volume of the canister 44. Setting the waste threshold level to a lower volume or lower relative the volume of the canister 44 can minimize risk of overflow of the toxic medical waste from the canister 44 to protect the patient 30 and hospital personnel. Similarly, the waste threshold level may be set higher or lower based upon viscosity of the medical waste, temperature of the medical waste, or any other suitable property of the medical waste or the surgical procedure. The controller 28 can be configured to send a signal to the suction motor 46 to stop suction and collection of the medical waste when the waste threshold is reached or exceeded. In some embodiments, the waste sensor 62 is configured to send a raw waste level signal to the controller 28, and the controller 28 is configured to determine when the amount of the medical waste has reached the threshold level. The raw waste level signal is an electric signal indicative of the amount of the medical waste contained in the canister 44. The indicator 60 can display indicia corresponding to the raw waste level signal such that the user can learn the amount of the medical waste sensed by the waste sensor 62 by looking at the indicator 60. The amount of the medical waste can be measured based upon volume, weight, or any other suitable metric. In some embodiments, the controller 28 is also configured to set the waste threshold level automatically or in response to input by the user.

The assembly 20 includes an energy storage device 64 and an energy storage device sensor 66. The energy storage device 64 and the energy storage device sensor 66 are each in communication with the controller 28. The energy storage device 64 is configured to provide electric power to the controller 28, the powered wheel 40, the suction pump 46, the vacuum regulator 47, and/or any other components of the assembly 20 that require electric power to function. In some embodiments, the assembly 20 includes a plurality of energy storage devices 64, each of the energy storage devices 64 providing electric power to one or more of the controller 28, the powered wheel 40, the suction pump 46, the vacuum regulator 47, and any other components of the assembly 20 that require electric power to function. The controller 28 can route and regulate the electric power to the other components of the assembly 20 that require electric power to function. For example, the energy storage device 64 can supply power to the controller 28 and the controller 28 can route a portion of the electric power to the suction motor. The controller 28 can further regulate function of the suction motor by regulating an amount of energy supplied to the suction motor, thereby increasing or decreasing suctioning power of the suction motor. The energy storage device 64 can be a battery, a capacitor, or any other suitable device for storing electric power.

The energy storage device sensor 66 is configured to sense a characteristic of the energy storage device 64. The characteristic of the energy storage device 64 can be a charge level, i.e., a measure of electric energy stored in the energy storage device 64. The characteristic of the energy storage device 64 can be a power level, i.e., a measure of the electric power supplied by the energy storage device 64. The energy storage device sensor 66 is configured to provide an energy storage device characteristic signal to the controller 28. The controller 28 is configured to initiate a charging protocol to be described when the energy storage device characteristic is below an energy storage device characteristic threshold. The energy storage device characteristic threshold can be, for example, configured relative a maximum electric power capacity of the energy storage device 64, e.g., 5% of the capacity or 20% of the capacity. Additionally, the energy storage threshold can be configured according to expected electric power usage. For example, a scheduled medical procedure that is expected to use a relatively large amount of electric power may require lowering the energy storage threshold to allow relatively more power usage before the assembly 20 initiates charging or prompts the user to initiate a charging protocol with the controller 28. The energy storage threshold can be a preset threshold level configured during manufacture and/or programming of the assembly 20. The energy storage threshold can otherwise, or additionally, be a threshold level configurable by hospital personnel or the user before, during, or after the medical procedure. The energy storage device sensor 66 can include an energy storage controller (not shown) configured to facilitate sensing of the characteristic of the energy storage device. In some embodiments, the energy storage device sensor 66 is configured to provide an energy storage threshold signal to the controller 28 when the characteristic of the energy storage device 64 sensed by the energy storage device sensor 66 meets the energy storage device characteristic threshold. The energy storage device characteristic threshold can be a level of electric power stored in the energy storage device 64 that is indicative of the energy storage device 64 being near an uncharged state and therefore necessitating transferring of electric power to the energy storage device 64 before more of the medical waste is collected. In some embodiments, the energy storage device characteristic threshold is stored in the memory component 56. In some embodiments, the energy storage device sensor 66 is configured to send a raw energy storage device characteristic signal to the controller 28, and the controller 28 is configured to determine when the amount of electric power stored in the energy storage device 64, state of charge, voltage, and/or other suitable electrical parameter has reached the threshold level. The raw energy storage device characteristic signal is an electric signal indicative of the amount of the electric power stored in the energy storage device 64, or some other indicator of the performance of the energy storage device. In some embodiments, the controller 28 is also configured to set the energy storage threshold automatically or in response to input by the user.

As previously described, the assembly 20 receives the medical waste during the medical procedure, with the medical waste being stored in the canister 44. The canister 44 has a fixed volume, and the volume fills with the medical waste during or after one or more medical procedures. Therefore, the canister 44 needs to be emptied of the medical waste during or after one or more medical procedures to prepare for collecting additional medical waste during future medical procedures. As such, the assembly 20 is configured to execute a waste disposal protocol for autonomously disposing of the medical waste contained in the canister 44. The waste disposal protocol is a series of steps executed by components of the assembly 20 for autonomously navigating the assembly 20 to the disposal station 50, establishing fluid communication between the disposal station 50 and the canister 44, and emptying and cleaning the canister 44 at the disposal station via the fluid communication. Consequently, it is not necessary for the hospital personnel to suspend their duties to carry or wheel the assembly 20 to the disposal station 50 to empty and clean the canister 44. The waste disposal protocol can include additional steps, to be described.

Furthermore, the assembly 20 is portable and the electric components of the assembly 20 are at least partially powered by the energy storage device 64, and thus the assembly 20 requires recharging of electric power stored in the energy storage device 64 during or after one or more medical procedures to prepare for collecting additional medical waste during the future medical procedures. For example, the following components of the assembly 20 can require electric power to function: the controller 28, the powered wheel 40, the motor 42, the suction pump 46, the vacuum regulator 47, the memory component 56, the indicator 60, the waste sensor 62, and the user input device 68. Additionally, some components of the assembly 20 to be described may require electric power to function. A finite amount of electric power is stored in the energy storage device, and the electric power is drained during use of the assembly, such as while collecting waste during the medical procedure or while navigating to the disposal station. As such, the energy storage device 64 requires recharging.

The execution of the waste disposal protocol by the assembly 20 may include the assembly 20 receiving electric power. Additionally, in some embodiments to be described, the assembly 20 is configured to execute the charging protocol for autonomously receiving electric power concurrently with executing the waste disposal protocol for disposing of the medical waste. In some embodiments, the assembly 20 is configured to execute the charging protocol for autonomously receiving electric power separately from executing the waste disposal protocol. In some embodiments, the controller 28 is configured to initiate the waste disposal protocol according to signals received from the waste sensor 62. For example, the controller 28 can be configured to initiate the waste disposal protocol if the raw waste level signal indicates that the amount of the medical waste contained in the canister 44 is above the waste threshold. Similarly, the controller 28 can be configured to initiate the waste disposal protocol upon receiving the raw waste level signal and the energy storage device characteristic signal and comparing the waste level signal and the energy storage device characteristic signal with the waste level threshold and the energy storage threshold, respectively. The controller 28 can also be configured to initiate the charging protocol upon, for example, receiving the energy storage device characteristic signal or comparing the energy storage device characteristic signal with the energy storage threshold.

The controller 28 may be configured to initiate one of the waste disposal and the charging protocol in response to receiving the user input signal on a user input device 68. The user input device 68 may be coupled to the base 22 and in communication with the controller 28. The user input device 68 can be, for example, a button, a switch, a toggle, a lever, a touch pad, a screen with touch controls, or a combination thereof. In certain embodiments, the user input device 68 may be a remote or mobile device, such as a smartphone, tablet, and the like, that may be carried by a user, and separable from the assembly. In some embodiments, the assembly 20 includes a plurality of user input devices 68. In some embodiments, the user input device 68 is remote from the assembly 20 and configured to wirelessly communicate with the controller 28. The user input device 68 is configured to provide a user input signal to the controller 28 in response to being actuated by a user. For example, during a surgical procedure the amount of medical waste stored in the canister 44 may reach the waste level threshold. The indicator 60 can alert a user that the waste level threshold has been reached, such as by blinking or displaying a light, beeping, displaying a message, vibration, or any other suitable indication. The user can actuate the user input device 68 when suitable, such as when medical procedure has concluded or when another assembly 20 is available to replace the assembly 20 in collected the medical waste, thereby initiating the disposal procedure or the charging procedure to empty and clean the canister 44 or to charge the energy storage device 64, respectively. In embodiments where the assembly 20 includes a plurality of user input devices 68, one of the user input devices 68 can provide a first user input signal to the controller 28 and other of the user input devices 68 can provide a second user input signal to the controller 28. The controller 28 can be configured to initiate the waste disposal protocol in response to receiving the first user input signal and to initiate the charging protocol in response to receiving the second user input signal.

Figure 2:
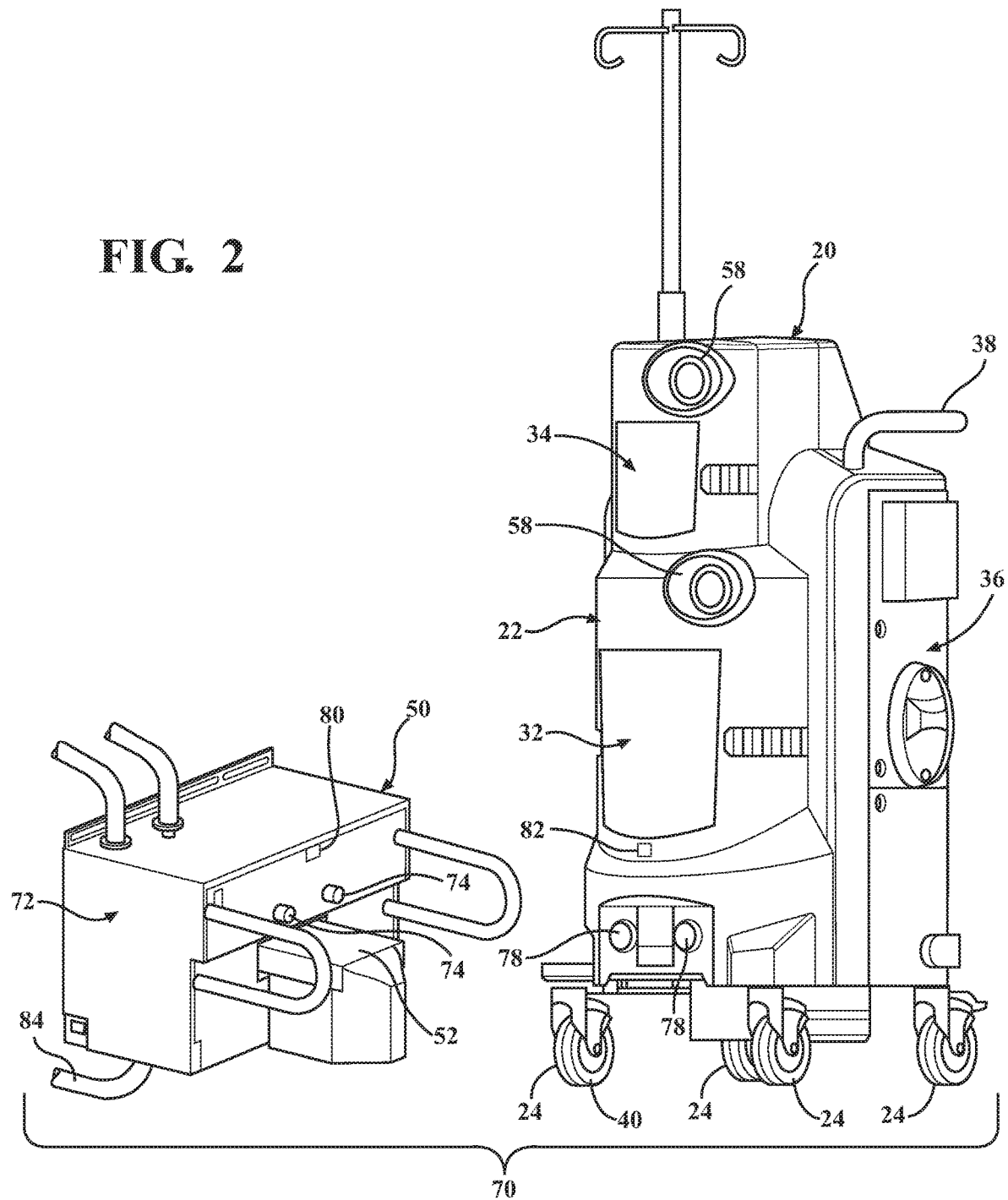
FIG. 2 is a perspective view of an embodiment of a medical waste collection system including the autonomous medical waste collection assembly and a disposal station.
Figure 3:
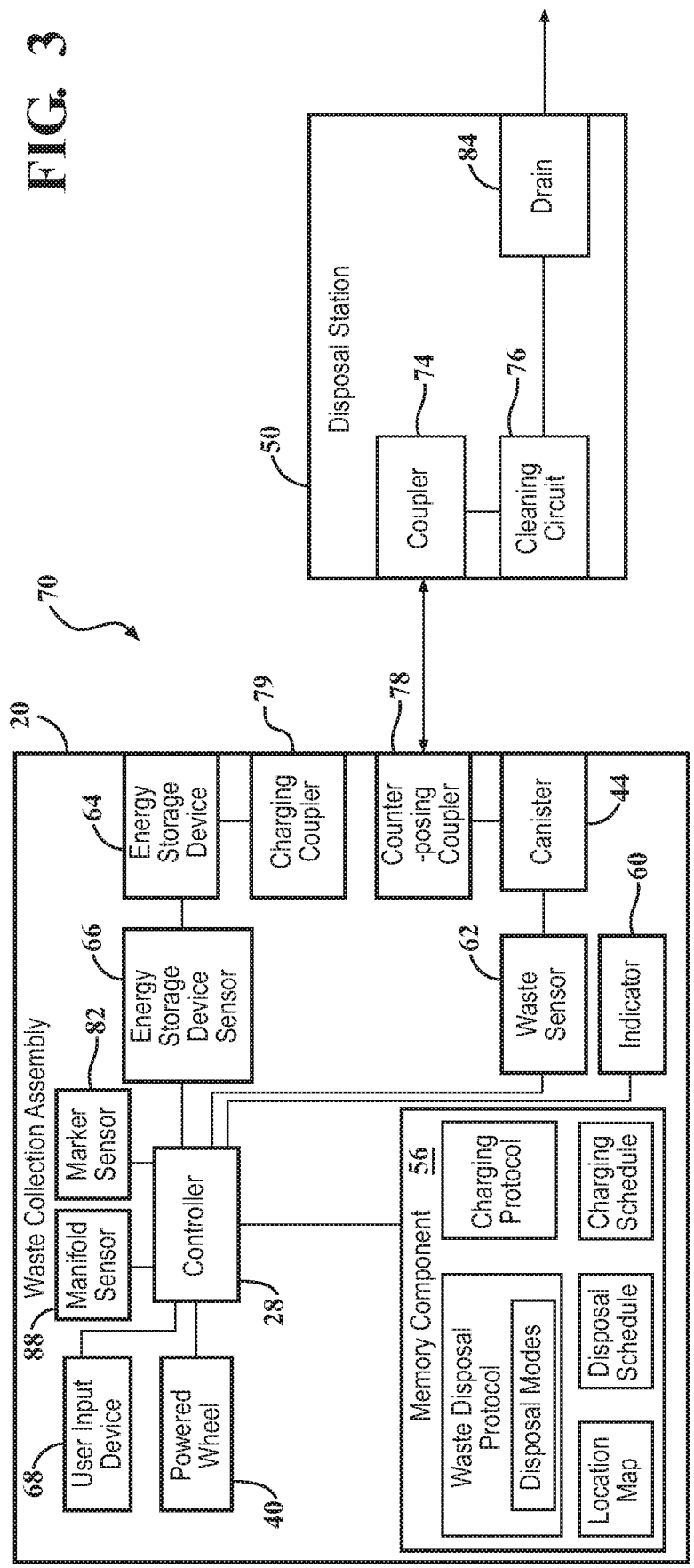
FIG. 3 is a block diagram of an embodiment of the medical waste collection system including the autonomous medical waste collection assembly and the disposal station.

Referring to FIGS. 2 and 3, in some embodiments the assembly 20 is part of a medical waste collection system 70. The medical waste collection system 70 includes a disposal station 50 configured to clean the canister 44 and remove the medical waste from canister 44, thereby sanitizing and emptying the canister 44. The disposal station includes a cleaning circuit 76 configured to clean the canister 44, for example by pumping water, detergent, and/or soap into the canister 44. In particular, the disposal station 50 is configured to clean and empty the canister 44 by creating a closed environment between the canister 44 and the disposal station 50, thereby reducing risk of hazardous or toxic materials from coming into contact with hospital personnel or patients 30. The disposal station 50 is configured to empty the canister 44 by receiving the medical waste from the canister 44 through a waste conduit 52. The waste conduit 52 creates a fluid connection with the assembly 20. The disposal station 50 is configured to clean the canister 44 of the assembly 20 by transferring water, soap, detergent, disinfectant, a combination thereof, or any other suitable cleaning or disinfecting substance into the canister 44 via the waste conduit 52. The disposal station 50 can be situated outside of an operating room, such as in a hallway or closet of the health care facility. Alternatively, the disposal station 50 can be situated inside an operation room.

With continued reference to FIGS. 2 and 3, the disposal station 50 may include a housing 72 and a coupler 74. As illustrated, the coupler 74 is coupled to the housing 72. The assembly 20 includes a counterposing coupler 78. The counterposing coupler 78 is coupled to the base 22. During the waste disposal protocol, the coupler 74 couples with the counterposing coupler 78 to align the assembly 20 with the waste conduit 52 such that the medical waste can be transferred from the canister 44 via the waste conduit 52. In some embodiments, the disposal station 50 includes a plurality of couplers 74 and the assembly 20 includes a plurality of counterposing couplers 78. FIG. 2 shows an embodiment of the system 70 including a plurality of couplers 74 and counterposing couplers 78 wherein the couplers 74 are located above the waste conduit 52 and the counterposing couplers 78 are located beneath the canisters 44 of the assembly 20. Gravitational force facilitates transfer of the medical waste from the canister 44 to the disposal station 50 via the waste conduit 52 when the couplers 74 and counterposing couplers 78 are coupled. In some embodiments, the coupler 74 includes a coupling electromagnet and the counterposing coupler 78 includes a counterposing coupling electromagnet in communication with the controller 28. The coupling and counterposing coupling electromagnets are configured to be selectively powered to form an attractive electromagnetic force between the coupler 74 and the counterposing coupler 78, thereby securely coupling the coupler 74 and the counterposing coupler 78 and aligning the assembly 20 and the waste conduit 52. One suitable electromagnetic coupling is disclosed in the aforementioned commonly owned U.S. Pat. No. 7,621,898 issued Nov. 29, 2009, the entire contents of which are hereby incorporated by reference. In other embodiments, the couplers 74 and counterposing couplers 78 can conversely or additionally include a mechanical interlocking mechanism, permanent magnets, or a combination thereof.

The assembly 20 is configured to autonomously dock with the disposal station 50. To facilitate the autonomous docking, in the illustrated embodiment, the disposal station 50 includes a marker 80 and the assembly 20 includes a marker sensor 82 in communication with the controller 28 to facilitate alignment of the coupler 74 and the counterposing coupler 78. As the assembly 20 navigates toward the disposal station 50, the assembly 20 must orient and align the counterposing coupler 78 with the coupler 74 in order to execute the disposal protocol. As such, the marker 80 can be disposed near the coupler 74 and the marker sensor 82 can be disposed near the counterposing coupler 78. The marker sensor 82 is configured to sense the marker 80 and send signals to the controller 28 indicative of the relative position of the marker sensor 82 to the marker 80. The controller 28 is configured to send signals to the powered wheel 40 to adjust facing, orientation, velocity, or any other necessary property of the assembly 20 in order to bring the marker sensor 82 in close proximity with the marker 80, thereby facilitating coupling of the coupler 74 and the counterposing coupler 78 for execution of the disposal protocol. The marker 80 can be an infrared marker, an NFC antenna, an emitter, a colored marker, or any other suitable marker. The marker sensor 82 can be an infrared sensor, an antenna, light sensor, or any other suitable marker sensor. It is also contemplated that the marker 80 may be disposed on the assembly 20, and the marker sensor 82 may be disposed on the disposal station 50, with the controller 28 of the assembly 20 being in wireless communication with a controller of the disposal station 50.

In some embodiments, the disposal station 50 includes a canister (not shown). The canister of the disposal station 50 is in fluid communication with the waste conduit 52 and adapted to receive the medical waste from the assembly 20. The canister of the disposal station 50 is in fluid communication with the waste collection unit 26 via the waste conduit 52 when the assembly 20 is coupled with the disposal station 50. In embodiments where the disposal station 50 includes the canister, the disposal station 50 can be substantially mobile, i.e., the disposal station 50 can be moved between locations in the hospital without necessitating infrastructure change to the hospital, such as plumbing or electrical changes. In other embodiments, the disposal station 50 includes a drain 84. The drain 84 is adapted to receive the medical waste from the assembly 20 and transfer the medical waste externally to the disposal station 50, such as to a sewage line of the hospital.

Figure 4:
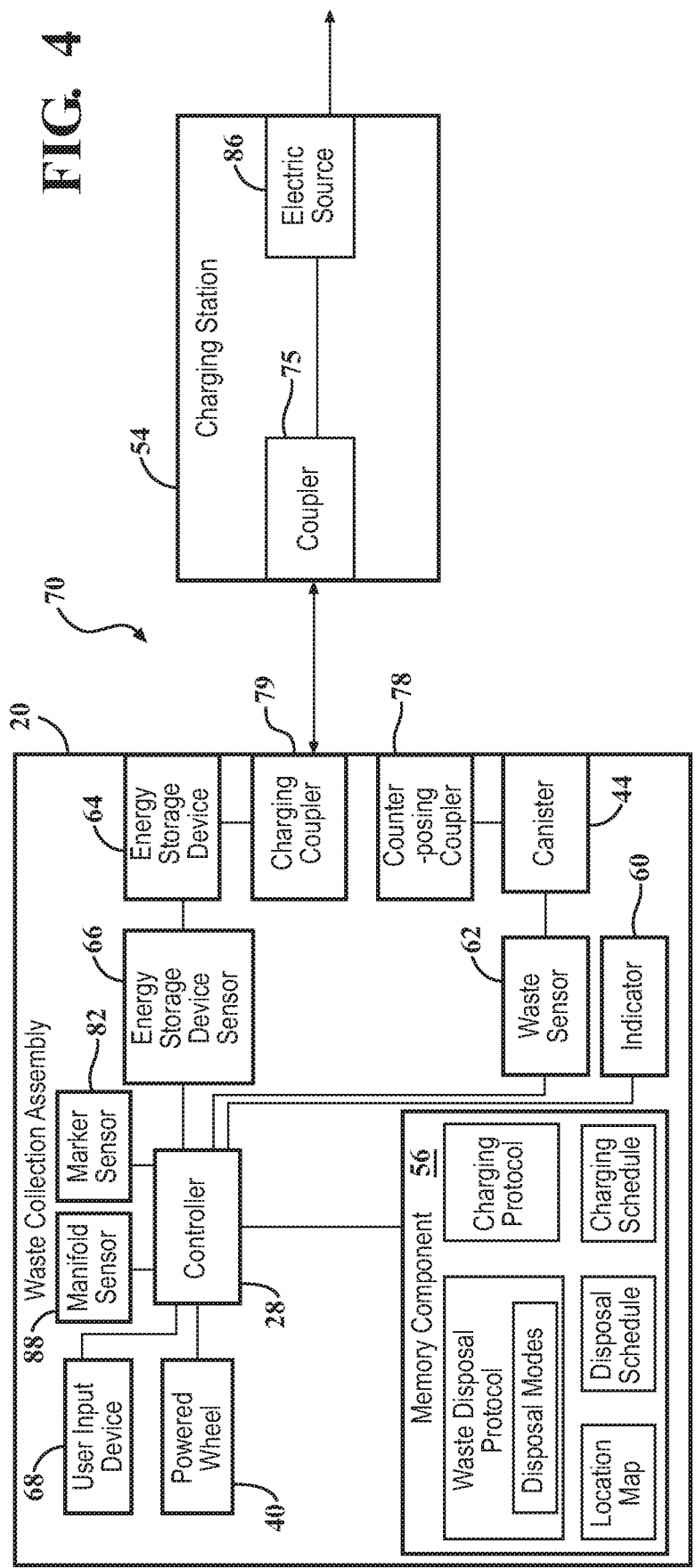
FIG. 4 is a block diagram of an embodiment of the medical waste collection system including the autonomous medical waste collection assembly and a charging station.

Referring to FIG. 4, the system 70 includes the charging station 54. The charging station 54 may be separate from the disposal station 50 and facilitates charging of the energy storage device 64. The charging station 54 is in electrical communication with an electric source. The electric source can be, for example, a power outlet, an uninterruptible power supply, a power conditioning system, a DC power system, or any other suitable type of electric source. The charging station 54 is configured to transfer electrical energy from the electric source to the energy storage device 64 when the assembly 20 is coupled with the charging station 54. The charging station 54 can be situated outside of an operating room, such as in a hallway of the health care facility. The charging station 54 can be situated inside an operation room (see FIG. 7), or in any other suitable location. In some embodiments, the charging station 54 is situated in one or more operating rooms of the medical facility or hospital. The assembly 20 can be configured to inductively receive electric power from the charging station 54 to charge the energy storage device 64 while the assembly 20 is being used to collect the medical waste during a surgical procedure.

The charging station 54 includes a housing and a coupler 75. The coupler 75 is coupled to the housing of the charging station 54. In some embodiments, during the charging protocol, the coupler 75 of the charging station 54 couples with a charging coupler 79 of the assembly 20 to align the assembly 20 with the charging station 54 such that the assembly 20 can receive electric power from the charging station 54. The coupler of the charging station 54 is substantially similar to the coupler 78 of the disposal station 50. The charging coupler 79 may include circuitry configured to enable electric communication between the energy storage device 64 and the charging station 54. The charging station 54 is configured to transfer electric power to the energy storage device 64 via the coupler 75 of the charging station and the charging coupler 79. The charging coupler 79 is configured to be removably coupled with the coupler 75 of the charging station 54 to receive electric energy from the charging station 54, thereby charging the energy storage device 64. For example, the couplers 75, 79 may be mechanically engaged (e.g., a plug) in order to provide an electrical connection between the charging station 54 and the assembly 20. For another example, the charging station 54 includes an inductive pad forming the coupler with the inductive pad configured to wirelessly transfer electrical energy from the electric source to the energy storage device 64.

Figure 5:
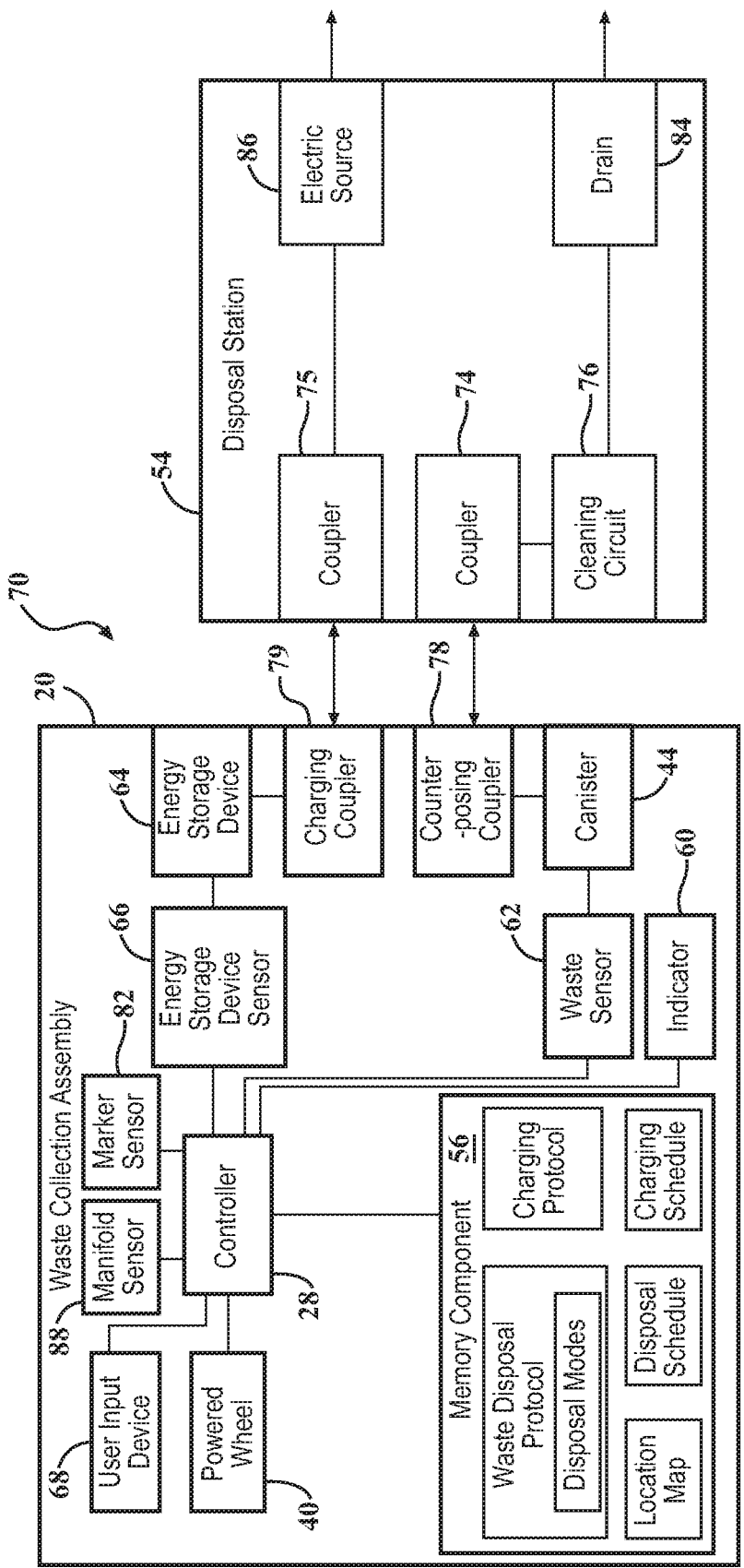
FIG. 5 is a block diagram of an embodiment of the medical waste collection system including the autonomous medical waste collection assembly and the disposal station with the disposal station including an electric source.

In some embodiments, the disposal protocol is complementary to the charging protocol. In other words, upon initiating the disposal protocol, the assembly 20 performs both of disposing of the medical waste and charging the energy storage device 64. Referring to FIG. 5, the disposal station 50 facilitates charging the energy storage device 64 while disposing of the medical waste and cleaning the canister 44. In the illustrated embodiment, the disposal station 50 is in electrical communication with an electric source. The disposal station 50 is configured to transfer electrical energy from the electric source to the energy storage device 64 when the assembly 20 is coupled with the disposal station 50. During the waste disposal protocol, the coupler of the charging station 54 couples with the charging coupler 79 to provide a connection between the assembly 20 and the charging station 54. The electric source can be, for example, a power outlet, an uninterruptible power supply, a power conditioning system, a DC power system, or any other suitable type of electric source. The electrically integrated disposal station 50 is configured to transfer electrical energy from the electric source to the energy storage device 64 when the assembly 20 is coupled with the charging station 54. In some embodiments, the disposal station 50 is configured to inductively transfer electric power to the assembly 20 to charge the energy storage device 64.

Upon initiation of the waste disposal protocol for reasons previously described (e.g., waste threshold signal, user input), the controller 28 sends several signals to components of the assembly 20 and the assembly 20 is configured to execute the waste disposal protocol according to the signals, thereby autonomously emptying and cleaning the canister 44 of the waste collection unit 26 at the disposal station 50 and, in some embodiments, autonomously charging the energy storage device 64 at the disposal station 50 and/or the charging station 54. Without limitation, the controller 28 is configured to send a waste disposal movement signal to the motor 42 connected to the powered wheel 40. The powered wheel 40 automatically moves the assembly 20 away from the patient 30 upon receiving the waste disposal movement signal. The powered wheel 40 automatically navigates the assembly 20 to the disposal station 50 after moving away from the patient 30.

The controller 28 may be configured to send a manifold signal to the indicator 60 upon initiation of the waste disposal protocol. Upon receiving the manifold signal, the indicator 60 is configured to prompt the user to remove the disposable manifold from the manifold receiver 58 and dispose of the disposable manifold upon receiving the manifold signal. The assembly 20 can include a manifold sensor in communication with the controller 28 and situated near the manifold receiver 58. The manifold sensor is configured to detect whether the disposable manifold is in contact with the manifold receiver 58. The controller 28 will only send the manifold signal to the indicator 60 if the manifold sensor detects that the disposable manifold is in contact with the manifold receiver 58. The controller 28 is configured to send the waste disposal movement signal after the disposable manifold is removed and disposed of.

The controller 28 may be further configured to prevent initiation of the waste disposal protocol during the medical procedure. More specifically, the controller 28 is configured to prevent initiation of the waste disposal protocol to prevent the assembly 20 from moving from the patient 30 while end effectors, suction lines 48, or other implements connected to the assembly 20 are in use to prevent movement of the assembly 20 and the end effectors, suctions tubes or other implements connected thereto away from the patient 30 from disrupting the surgical procedure. Prevention of the waste disposal protocol also prevents the assembly 20 from breaking a sterile field when moving away from the patient 30, thereby preserving sterility and safety during the medical procedure. For example, if the waste disposal protocol would otherwise be initiated in response to receiving the waste level signal from the waste sensor 62 or in response to determining that the amount of the medical waste has reached the threshold level, the controller 28 may delay providing the waste disposal signal until after the surgical procedure. In other words, the controller 28 is configured to prevent or delay initiation of the waste disposal protocol during the medical procedure unless the waste disposal protocol is initiated as a result of user input. For example, the controller 28 can be configured to delay providing the waste disposal signal while the suction pump 46 is actively suctioning waste. In some embodiments, the user can override prevention of initiation of the waste disposal protocol by actuating the user input device.

Similar to the waste disposal protocol, the controller 28 can be configured to prevent initiation of the charging protocol during the medical procedure if, for example, the controller 28 receives the energy storage device characteristic signal from the waste sensor 62 during the medical procedure. Among other advantages, the controller 28 prevents the assembly 20 from moving from the patient 30 while end effectors, suction lines 48, or other implements connected to the assembly 20 are in use and/or to avoid breaking a sterile field. In some embodiments, the user can override prevention of initiation of the charging protocol by actuating the user input device. Yet with initiation of the charging protocol prevented, for example during the medical procedure, it may be desirable or necessary to supply power to the assembly 20. For example, should the energy storage characteristic be undesirably low relative to anticipated remaining time (and corresponding energy consumption of the assembly 20) of the medical procedure, it will be necessary to supply power to the assembly 20 to, among other functions of the assembly 20, avoid inadvertent loss of suction from the suction pump 46. Therefore, in some embodiments, the assembly 20 includes an energy supply device (not shown) configured to receive power from an energy source and supply the power to the assembly 20. For example, the energy supply device may be a cord extending from any suitable structure of the assembly 20 such as the lower frame 32, the upper frame 34, or the vertical chassis 36. The base 22 can have any suitable shape. A plug at the end of the cord is configured to couple with an outlet associated with a station, for example the charging station 54, and/or a wall of the medical facility. Additionally or alternatively, the energy storage device 64 may be replaceable with another energy storage device 64. In one example, the energy storage device 64 is an external battery (e.g., a Lithium-ion battery) capable of being decoupled from the remainder of the assembly 20. Complementary contacts between the battery and a battery receiver are disengaged, and a replacement battery is disposed within the battery receiver with corresponding contacts engaged to supply the supply power to the assembly 20. In such a situation where energy supply device and/or the replacement energy storage device 64 is utilized, the controller 28 may be configured to provide a notification to, for example, a hub controller 96. In manners to be described, the hub controller 96 polls each of the controllers 28 of the additional assemblies to receive information regarding the amount of energy in each of the energy storage devices 64. The hub controller 96 can then select one of the additional assemblies to navigate to the duty station to relieve the assembly 20 with the purportedly lower energy storage characteristic. Moreover, the controller 28 may also provide a notification to the user.

The memory component 56 is configured to store a disposal schedule for scheduling initiation of the waste disposal protocol. Times to schedule initiation of the waste disposal protocol include, for example, an end of scheduled hours of surgery for an operating wing of a hospital, or a time prior to scheduled hours of surgery for an operating wing of the hospital. The controller 28 of the disposal station 50 is configured to initiate the waste disposal protocol as scheduled according to the disposal schedule. For example, a hospital may have an operating wing having several operating rooms staffed for scheduled operations between 9 a.m. and 5 p.m. The disposal schedule can include scheduled initiation of the waste disposal protocol at 8 a.m. and 5:30 p.m. in order to conveniently have the assembly 20 autonomously empty and clean the canister 44 of the assembly 20 and/or recharge the energy storage device 64 without the waste disposal protocol or the charging protocol conflicting with scheduled medical procedures. Any other suitable times may be scheduled in the disposal schedule for initiation of the waste disposal protocol, such as in between scheduled medical procedures. The controller 28 can be configured to initiate the waste disposal protocol without actuation of the user input if the waste disposal protocol is initiated during a scheduled time according to the disposal schedule. In some embodiments, the disposal schedule corresponds to a hospital network system, such as an operation scheduling system, a staff scheduling system, a resource management system, an electronic medical record (EMR), a combination thereof, or any other suitable hospital network system. The disposal schedule may be stored at other memory locations other than memory component 56. The EMR is a computer-based system for storage and transfer of hospital data such as patient data, resource data, device data, and other types of data relevant to operation of the hospital. Scheduled surgical procedures may be stored in the EMR and transferred from the EMR to the memory component 56 of the assembly 20 via a hospital network. The disposal schedule can be configured to correspond to the scheduled surgical procedures, such as by scheduling the waste disposal procedure to be initiated before the scheduled surgical procedures begin, after the scheduled surgical procedures end, between the surgical procedures, or a combination thereof. As such, the memory component may be dynamically linked to the EMR such that as new procedures are scheduled, the controller 28 appropriately initiates the charging and/or disposal protocol.

The memory component 56 is configured to store a charging schedule. The charging schedule includes one or more times to initiate the charging protocol. The controller 28 is configured to initiate the charging protocol according to the charging schedule. Similarly to the disposal schedule, the one or more times to initiate the charging can correspond to an end time of the medical procedure. For example, in some embodiments the charging schedule can correspond to a medical procedure schedule of an operating wing of a health care facility, the medical procedure schedule including beginning times and expected end times for each of the medical procedures. The charging schedule can correspond such that the controller 28 initiates the charging protocol at appropriate times between the medical procedures, thereby enabling the energy storage device 64 to be substantially charged as necessary for the medical procedures. In other embodiments, the charging schedule can correspond to an end of daily operations for the operating wing. The charging schedule can correspond such that the controller 28 initiates the charging protocol at or near the end of daily operations for the operating wing, thereby enabling the energy storage device 64 to be substantially charged before operations start on a following day. In some embodiments, the disposal schedule corresponds to a hospital network system such as the EMR.

At some times, the canister 44 of the assembly 20 needs to be emptied and cleaned quickly, for example in between or during scheduled medical procedures. However, quick emptying and cleaning of the canister 44 of the assembly can leave some amount of the medical waste and/or bacteria or toxic material in the canister 44 of the assembly. As such, at other times the canister 44 of the assembly 20 needs to be emptied and cleaned more thoroughly, such as overnight or after an end of day for a surgical wing. As such, in some embodiments, the waste disposal protocol includes a plurality of disposal modes. Each of the disposal modes includes a different amount of time the assembly 20 and the disposal station 50 are to be coupled while removing the medical waste from the waste collection unit 26. The controller 28 can be configured to automatically select one of the disposal modes. The controller 28 can select one of the disposal modes based on an amount of the medical waste within the waste collection unit 26, the amount of medical waste to be removed from the waste collection unit 26, a type of medical procedure that the assembly was used for, a type of medical waste inside the container, a length of time the medical waste has been stored in the canister 44, or a combination thereof. By way of non-limiting example, the waste disposal protocol can include a quick docking mode, a normal docking mode, and an extended docking mode. When the controller 28 initiates the waste disposal protocol with the quick docking mode, the assembly 20 can be configured to couple to the disposal station 50 for approximately five minutes. The quick docking mode is suitable for emptying and cleaning the canister 44 of the assembly in between or during medical procedures. When the controller 28 initiates the waste disposal protocol with the normal docking mode, the assembly 20 can be configured to couple to the docking station for approximately thirty minutes, thereby more effectively emptying and cleaning the canister 44 of the assembly than the quick docking mode. The normal docking mode is suitable for emptying and cleaning the canister 44 of the assembly before or after a scheduled day of medical procedures, such as at morning or at night. When the controller 28 initiates the waste disposal protocol with the extended docking mode, the assembly 20 can be configured to couple to the disposal station 50 for approximately two hours, thereby more effectively emptying and cleaning the canister 44 of the assembly than the quick or normal docking modes. The extended docking mode is suitable for periodically emptying and cleaning the canister 44 of the assembly, such as weekly, biweekly, monthly, quarterly, or biannually. The above identified times for each of the modes are merely exemplary with any length of time for each of the modes being contemplated by the present disclosure.

In some embodiments, the disposal modes also include different types or amounts of disinfectant or detergent to be used by the disposal station 50 to clean the canister 44 of the assembly during the waste disposal protocol. The controller can automatically select the amounts and/or types of disinfectants or detergents based on the type of medical waste collected, or a type of procedure that the assembly was used for, for example, some medical procedures collect large amounts of blood while other medical procedures collect large amounts of saline. The controller 28 can use a sensor to determine a type and/or amount of medical waste, such as determining that a large amount of blood has been collected or that the assembly 20 is used in a medical procedure during which large amounts of blood are typically collected. In response, the controller 28 can initiate the waste disposal protocol with a disposal mode using disinfectants and/or detergents appropriate for cleaning large amounts of blood from the canister 44 of the assembly.

The controller 28 may be configured to select one of the disposal modes based on a user input or the disposal schedule, thereby allowing a user to select one of the disposal modes while initiating the disposal procedure. In embodiments where the assembly 20 includes a plurality of user inputs, each of the user inputs can be configured to enable the controller 28 to initiate the waste disposal protocol with a different disposal mode of the plurality of disposal modes. For example, one of the user inputs can be configured to enable to controller 28 to initiate the waste disposal protocol with the quick disposal mode upon actuation of the one user input. Other of the user inputs can be configured to enable the controller 28 to initiate the waste disposal protocol with the normal disposal mode upon actuation of the other user input. Still another of the user inputs can be configured to enable the controller 28 to initiate the waste disposal protocol with the extended disposal mode upon actuation of the other user input. In some embodiments, a user can actuate the user input device 68 to configure one or more of the disposal modes. For example, the user can actuate one user input of the user input device 68 to configure the quick disposal mode to run for three minutes, and actuate another user input of the user input device 68 to initiate the disposal protocol with the quick disposal mode. Configurations of the disposal modes may be stored in the memory component 56.

Figure 6:
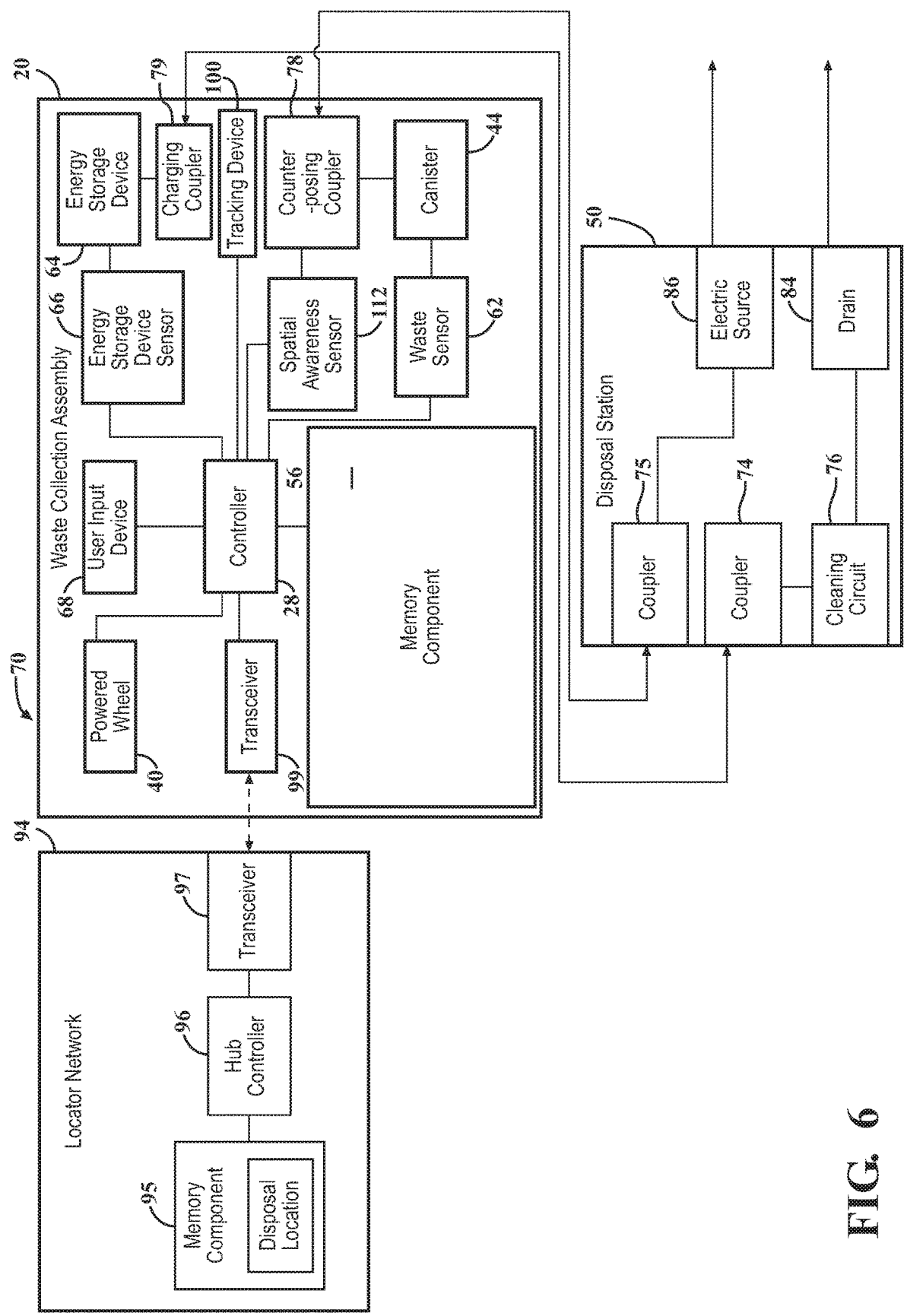
FIG. 6 is a block diagram of an embodiment of the medical waste collection system including the autonomous medical waste collection assembly, the disposal station, and a locator network.
Figure 7:
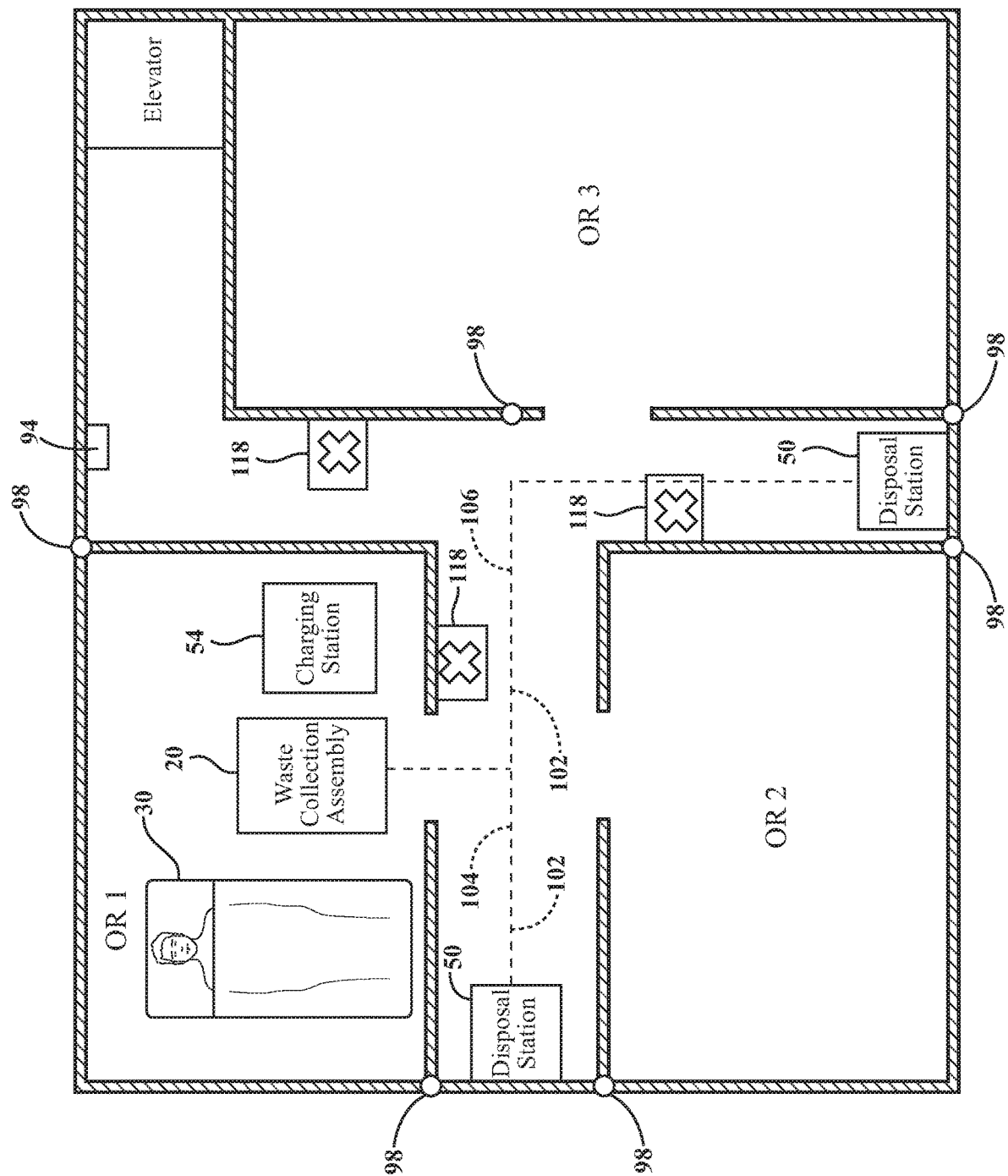
FIG. 7 is a schematic view of an exemplary operating wing of a medical facility including the autonomous medical waste collection assembly, a plurality of disposal stations, the charging station, and a locator network.

It is readily appreciated that the assembly 20 must be capable of performing autonomous movement to execute the aforementioned protocols, particularly movement within a complex and often crowded environment. Referring now to FIGS. 6 and 7, in some embodiments, a locator network 94 is configured to track position of the assembly 20 and position of the disposal station 50 and/or the charging station 54. FIG. 6 shows a block diagram of the locator network 94, the autonomous waste collection assembly 20, and the disposal station 50. Tracking position of the assembly 20 and position of the disposal station 50 and/or the charging station 54 facilitates the controller 28 navigating the assembly 20 to the disposal station 50 and/or the charging station 54. The locator network 94 can send signals to the assembly 20 enable the controller 28 to be aware of the position of the assembly 20, particularly within the medical facility. The locator network 94 can also send signals to the assembly 20 to enable the controller 28 to be aware of the position of the disposal station 50 and/or the charging station 54. The controller 28 is configured to navigate the assembly 20 to the disposal station 50 and/or the charging station 54 based upon signals received from the locator network 94. The locator network 94 can include a hub controller 96, a memory component 95, and a transceiver 97. The hub controller 96 is configured to execute computer-executable instructions to perform the functions of the locator network 94. The hub controller 96 can be a microprocessor, a microcontroller, a field programmable gate array (FPGA), a system on a chip (SoC), or any other suitable type of controller for executing the functions of the locator network 94. The memory component 95 of the locator network 94 is in communication with the hub controller 96 and is configured to store data and instructions related to functions of the locator network 94. The locator network 94 is configured to send signals to the assembly 20 and receive signals from the assembly via the transceiver 97. In some embodiments, the assembly 20 includes a transceiver 99 configured to send signals to the transceiver 97 of the locator network 94 and receive signals from the transceiver 97 of the locator network 94.

The medical waste collection system 70 includes a plurality of locator sensors 98 in communication with the locator network 94. The locator sensors 98 can be in wired or wireless communication with the locator network 94. The locator sensors 98 can be optical, infrared, sonographic, or any other suitable detection-based technology configured to wirelessly detect a device at a distance. The locator sensors 98 can be mounted to walls and/or the ceiling within hallways of the medical facility, or can be situated at any other suitable position within the medical facility. FIG. 7 shows an exemplary layout of the locator sensors 98 situated in an operating wing of a hospital. The locator sensors 98 can be configured to detect a tracking device coupled to the assembly 20. Further, the locator sensors 98 can be configured to detect a tracking device of the disposal station 50 and/or the charging station 54. The tracking devices can include, for example, GPS units and RFID chips. The controller 28 is configured to receive a current location input signal and a disposal location input signal from the locator network 94 within the medical facility. The current location input signal is based on a current location of the assembly 20. The disposal location input signal is based on a disposal location of the disposal station 50. In some embodiments, the controller 28 is configured to receive a charging location input signal from the locator network 94 within the medical facility. The charging location input signal is based on a charging location of the charging station 54.

The controller 28 is configured to navigate the assembly 20 to the disposal station 50 and/or the charging station 54 based on the current location input signal and the disposal location input signal. The controller 28 navigates the assembly 20 according to the current location input signal and the disposal location input signal and/or the charging location input signal. The controller 28 is configured to navigate the assembly 20 by selectively powering the motor 42 of the powered wheel 40 to move and steer the assembly 20 toward the disposal location and/or the charging location.

In some embodiments, the system 70 includes a plurality of disposal stations 50, as shown in FIG. 7, as well as one or more charging stations 54. The controller 28 may be further configured to receive a current location input signal as well as disposal location input signals for each of the disposal stations 50 and charging location input signals for each of the charging stations 54. Upon initiating the waste disposal protocol, the controller 28 is configured to navigate the assembly 20 to one of the disposal stations 50 according to the corresponding disposal location input signal. The controller 28 can decide to which of the disposal stations 50 to navigate based on factors such as distance, time, and whether another assembly 20 is already performing the waste disposal protocol at one or more of the disposal stations 50. For example, the system 70 can include first and second paths 104, 106 to the disposal stations 50. The controller 28 may be configured to use decision-making logic to determine whether to navigate to the first path 104 or the second path 106. The controller 28 may decide to navigate to the first path 104 rather than the second path 106 due to a lesser distance between the assembly 20 and the disposal station 50 via the first path 104 compared to a greater distance between the assembly 20 and the disposal station 50 via the second path 106.

With continued reference to FIG. 7, in some embodiments the memory component 56 is configured to store a location map. The location map includes a layout of at least a portion of the medical facility, the layout being comprehensible by the controller 28. The controller 28 selectively powers the motor 42 by calculating a trajectory based upon the current location input signal and the disposal location input signal and/or the charging location input signal with respect to the location map. The controller 28 is configured to selectively power the motor 42 to follow the trajectory. The controller 28 is configured to calculate the trajectory based upon the current location input signal and the disposal location input signal when the waste disposal protocol is initiated such that the controller 28 navigates the assembly 20 to the disposal station 50. Alternatively, the controller 28 is configured to calculate the trajectory based upon the current location input signal and the charging location input signal when the charging protocol is initiated such that the controller 28 navigates the assembly 20 to the charging station 54.

In some embodiments, the memory component 56 is configured to store a plurality of defined paths 102 within the medical facility. The defined paths 102 are predefined paths, for example, paths along one or more hallways of an operating wing of a hospital, between locations in the medical facility. The defined paths 102 can be predefined paths between operating rooms and the disposal station 50 and/or the charging station 54. The controller 28 is configured to navigate the assembly 20 to the disposal station 50 and/or the charging station 54 along one of the defined paths 102. The controller 28 is configured to navigate the assembly 20 to the disposal station 50 and/or the charging station 54 based on a distance between the current location and the disposal location. For example, the defined paths 102 can include the first path 104 between an operating room and a first disposal station 50 and the second path 106 between the operating room and a second disposal station 50. Upon initiating the waste disposal protocol, the controller 28 can determine whether the assembly 20 is positioned at the first operating room or the second operating room based on the current location input signal. The controller 28 can determine whether to navigate the assembly 20 to the first disposal station 50 along the first path 104 or to the second disposal station 50 along the second path 104. In some embodiments, the defined paths 102 include a plurality of paths between each of the operating rooms and each of the disposal stations 50 and/or charging stations 54.

One or more spatial awareness sensors 112 may be provided and in communication with the controller 28. An embodiment of the assembly 20 including one spatial awareness sensor 112 is described herein for simplicity of description. The spatial awareness sensor 112 is configured to sense objects obstructing the assembly 20 while the assembly 20 is navigating to the disposal station 50 and/or the charging station 54, such as along one of the defined paths 102. The spatial awareness sensor 112 can be a capacitive sensor, a capacitive displacement sensor, a Doppler Effect sensor, an eddy-current sensor, an inductive sensor a magnetic sensor, an optical sensor, a radar device, a sonar device, a lidar device, a combination thereof, or any other suitable type of sensor. The controller 28 is configured to direct the assembly 20 to deviate from the path in response to the sensed obstruction 118. After deviating from the path, the controller 28 is configured to navigate the assembly 20 around the obstruction 118 to continue to the destination, i.e., the disposal station 50 or the charging station 54, once the assembly 20 has navigated around the obstruction 118. The controller 28 can determine that the obstruction 118 cannot be navigated around, in which case the controller 28 is configured to determine an alternate path to the disposal station 50 or the charging station 54, or to navigate to a different disposal station 50 or charging station 54. The sensed obstruction 118 can be, for example, a doctor, a nurse, other hospital personnel, a patient 30, a wheelchair, a hospital bed, a cabinet, or any other obstruction 118 that may be present in the medical facility. Upon sensing the obstruction 118, the controller 28 is configured to direct the assembly 20 to deviate in order to prevent the assembly 20 from colliding with the sensed obstruction 118 while navigating to the disposal station 50 and/or the charging station 54 during the waste disposal protocol or the charging protocol. In some embodiments, the spatial awareness sensor 112 is also configured to assist in aligning the assembly 20 with the disposal station 50. For example, the spatial awareness sensor 112 can detect location of the disposal station 50 relative the assembly 20 when the assembly 20 is near the disposal station 50. The controller 28 can then send signals to the motor 42 of the powered wheel 40 to bring the counterposing coupler 78 near the coupler 74 based upon the signals from the spatial awareness sensor 112.

It is readily appreciated that the autonomous movement of the assembly 20 and the additional automated features of the system 70 of the present disclosure advantageously relieves hospital personnel from suspending their duties to carry out many tasks previously incumbent on them to perform. In certain situations, however, it may be desirable to operate the assembly 20 in the absence of the autonomous movement and/or automated features. In other words, it may be desirable for the user to "opt out" of an autonomous mode to operate the assembly 20 in what may be considered a manual mode. Exemplary instances or situations where the manual mode may be desired include servicing the assembly 20, "one off" or unexpected uses, repositioning of the assembly 20 within the medical facility or more particularly the operating room, and avoiding congestion within hallways of the medical facility during especially busy times. For example, it may be necessary to reposition the assembly 20 within the operation room, and the powered wheel 40 may provide resistance to such movement. As opposed to programming or inputting the needed movement, it may be easier to simply maneuver the assembly 20 manually to the desired position. The actuation of the assembly 20 between the autonomous and manual modes may include the user input device 68 receiving an input from the user. In the autonomous mode, for example, the assembly 20 may include engagement of a clutch mechanism 49 (see FIG. 1) with the motor 42 of the powered wheel 40 that prevents the user from manually moving (e.g., pushing) the assembly 20 along the floor surface. The clutch mechanism 49 is in communication with the controller 28 and the user input device 68. As the assembly 20 moves from the autonomous mode to the manual mode, the clutch mechanism 49 may disengage from the motor 42 to permit the powered wheel 40 to move freely along with remaining wheels 24 of the assembly 20. In another example, provided adequately stability is maintained by the assembly 20, a lift mechanism 51 (see FIG. 1) coupled to the powered wheel 40 and in communication with the controller 28 and the user input device 68. As the assembly 20 moves from the autonomous mode to the manual mode, for example consequent to an input to the user input device 68, the lift mechanism 51 moves the powered wheel 40 away from the floor surface such that the powered wheel 40 is no longer contacting the same. Should the remaining wheels 24 be non-powered, the assembly 20 may be manually moved freely along the floor surface. The assembly 20 may be repeatedly moved between the autonomous and manual modes as desired.

Figure 8:
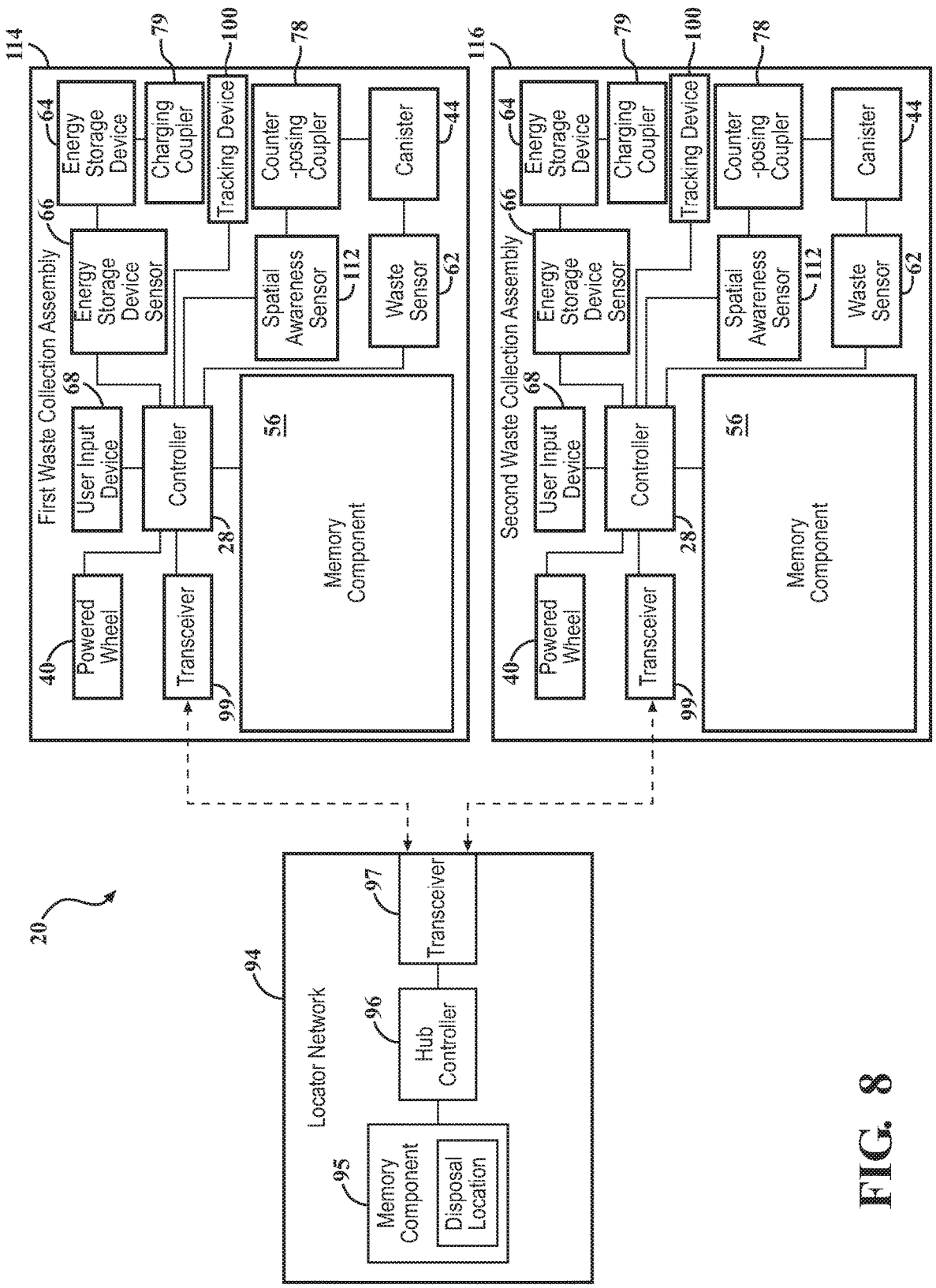
FIG. 8 is a block diagram of an embodiment of the medical waste collection system including first and second autonomous medical waste collection assemblies and the locator network.
Figure 9:
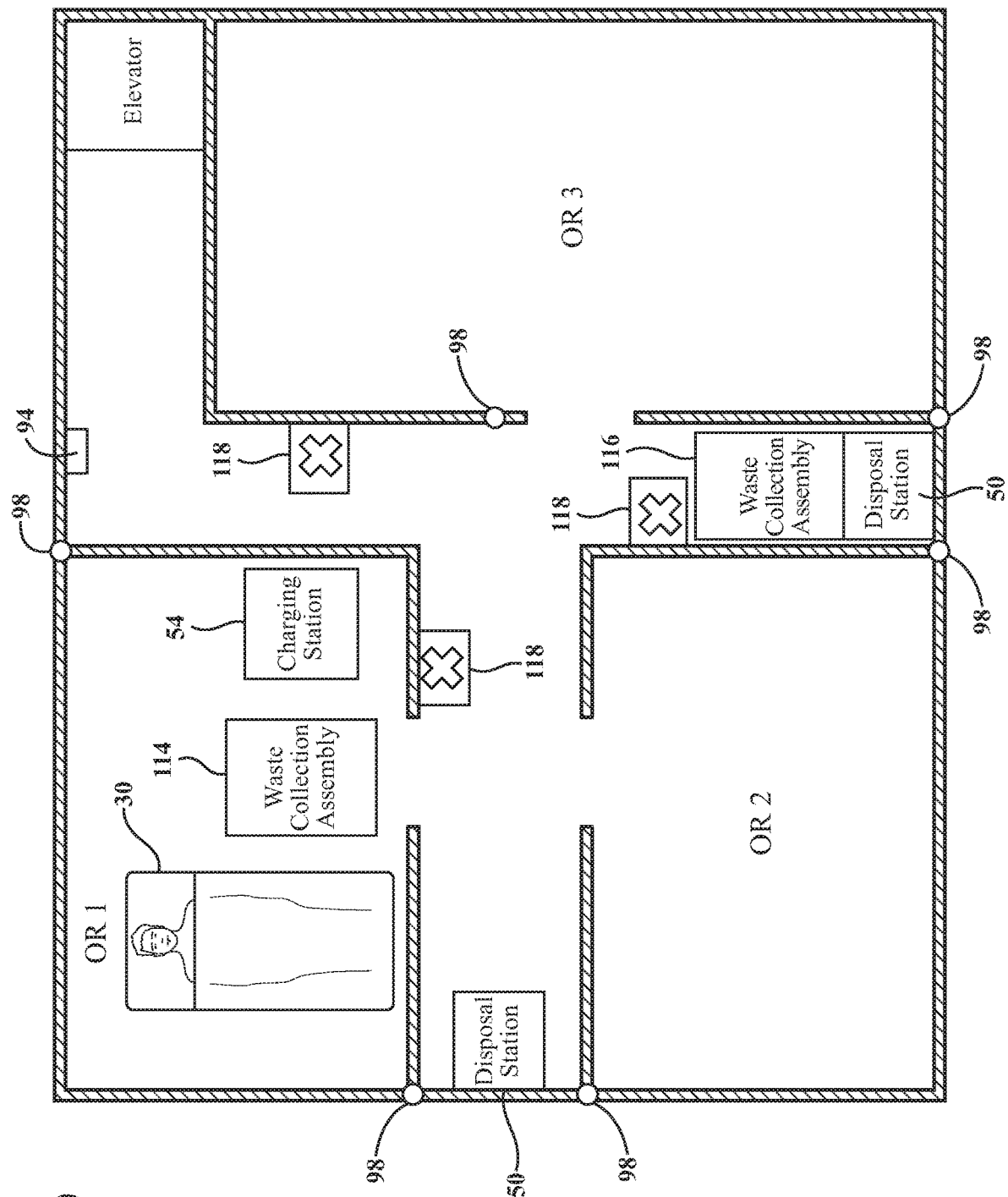
FIG. 9 is a schematic view of another exemplary operating wing of a medical facility including the first and second autonomous medical waste collection assemblies, the plurality of disposal stations, the charging station, and the locator network.

Referring to FIGS. 8 and 9, in some embodiments, the assembly 20 is a first autonomous medical waste collection assembly 114 and the medical waste collection system 70 includes a second autonomous medical waste collection assembly 116. The second assembly 116 includes a base, a plurality of wheels coupled to the base and including a powered wheel, a waste collection unit coupled to the base and including a canister and a suction pump in fluid communication with the canister, a vacuum regulator in communication with the suction pump, a counterposing coupler coupled to the base, and a controller. The base, the plurality of wheels, the waste collection unit, the counterposing coupler 78, and the controller of the second assembly 116 may be configured similarly to the base 22, the plurality of wheels 24, the waste collection unit 26, the counterposing coupler 78, the charging coupler 79, and the controller 28 of the first assembly 114. The second assembly 116 may be substantially similar to the first assembly 114 in both structure and function.

The disposal stations 50 and the charging station 54 can each only facilitate execution of the disposal procedure for a limited number of the assemblies simultaneously. For example, in some embodiments, only one of the assemblies 114, 116 can be coupled with each of the disposal stations 50 at a time. As such, for example, the first assembly 114 coupled with the disposal station 50 must decouple from the disposal station 50 before the second assembly 116 can couple with the disposal station 50 to execute the disposal protocol. If the controller 28 of the first assembly 114 initiates the disposal protocol while the second assembly 116 is executing the disposal protocol, a conflict may occur where the second assembly 116 is occupying the disposal station 50 to which the controller 28 of the first assembly 114 is trying to navigate the first assembly 114 to execute the disposal protocol. Similarly, if the controllers 28 of the first and second assemblies 114, 116 initiate the disposal protocol at similar times, a conflict may occur where each of the first and second assemblies 114, 116 are navigating the first and second assemblies 114, 116, respectively, to execute the disposal protocol at the disposal station 50. Similar issues may arise with regard to the charging stations 54. To resolve such conflicts, in some embodiments, the first and second assemblies 114, 116 are each adapted to be removably coupled to the charging in an interchangeable manner such that the first and second assemblies 114, 116 form a queue if waste disposal protocols of the first and second assemblies 114, 116 have each been initiated and are concurrently active. The queue facilitates one or more of the assemblies 114, 116 waiting until other of the assemblies 114, 116 have finished executing the disposal protocol before coupling with the disposal station 50. The queue can be stored in one or more of the memory components 56 of the assemblies 114, 116, the memory component of the locator network 94, or a combination thereof. Likewise, in certain embodiments, a singular one of the first and second waste assemblies 114, 116 can be coupled to the charging at one time. In such embodiments, the controller of the second assembly 116 is configured to queue if the first assembly 114 is positioned at the charging station 54. The second assembly 116 can queue by suspending the charging protocol of the second assembly 116 and waiting until the first assembly 114 has completed the charging protocol of the first assembly 114 before reinitiating or resuming the charging protocol of the second assembly 116. The second assembly 116 can navigate near or adjacent to the charging station 54 before suspending the waste disposal protocol of the second assembly 116.

The locator network 94 is configured to track location of each of the first and second assemblies 114, 116 as well as any number of disposal stations 50 and/or charging stations 54. The locator network 94 is configured to send signals to the controllers of each of the first and second assemblies to make each of the first and second assemblies 114, 116 aware of locations of other of the first and second assemblies 114, 116. In some embodiments, the controller of the second assembly 116 is configured to receive a first location input signal and a second location input signal from the locator network 94. The first location input signal is based on a first location of the first assembly 114. The second location input signal is based on a second location of the second assembly 116. In some embodiments, the first and second assemblies are each adapted to be removably coupled to the disposal station 50 in an interchangeable manner such that the first and second assemblies 114, 116 form a queue if waste disposal protocols of the first and second assemblies 114, 116 have each been initiated and are concurrently active. In certain embodiments, a singular one of the first and second waste assemblies 114, 116 can be coupled to the disposal station 50 at one time. In such an embodiment, the controller 28 of the second assembly 116 is configured to queue if the first assembly 114 is positioned at the disposal station 50. The second assembly 116 can queue by suspending the waste disposal protocol of the second assembly 116 and waiting until the first assembly 114 has completed the waste disposal protocol of the first assembly 114 before reinitiating or resuming the waste disposal protocol of the second assembly 116. The second assembly 116 can navigate near or adjacent to the disposal station 50 before suspending the waste disposal protocol of the second assembly 116.

When both of the first and second assemblies initiate the disposal protocol, the hub controller 96 may be configured to select one of the first and second assemblies 114, 116 to perform the disposal procedure. The other of the first and second assemblies 114, 116 that is not selected, can be queued behind the one of the first and second assemblies 114, 116 that is selected. The hub controller 96 selects the one of the first and second assemblies 114, 116 to perform the disposal procedure prior to the other one of the first and second assemblies 114, 116. The hub controller 96 may select the one of the first and second assemblies 114, 116 based on relative amounts of the medical waste in the waste collection units 26 of the first and second waste collection assemblies 114, 116. For example, the hub controller 96 can poll each of the controllers 28 of the first and second assemblies to receive information regarding the amount of the medical waste contained in each of the canisters of the first and second assemblies 114, 116. The hub controller 96 can then select one of the first and second assemblies 114, 116 to perform the waste disposal protocol based on the amount of medical waste in the waste collection unit. The hub controller 96 can instruct other of the first and second assemblies 114, 116 to navigate to an operating room to receive waste during a medical procedure. Similarly, the hub controller 96 can poll each of the controllers 28 of the first and second assemblies 114, 116 to receive information regarding the amount of energy in each of the energy storage devices 64 of the first and second assemblies. The hub controller 96 can then select one of the first and second assemblies 114, 116 to perform the charging protocol. The hub controller 96 can instruct other of the first and second assemblies 114, 116 to navigate to an operating room to receive waste during a medical procedure. The hub controller 96 may also control the queue for the charging protocol or the disposal protocol based on the disposal schedule, the charging schedule, the type of scheduled surgical procedure, the type of medical waste, etc.

At some times, it is expected that a user will initiate the disposal protocol for the first assembly 114 during a medical procedure and before completion of the medical procedure. As such, the second assembly 116 can be configured to navigate to the location of the first assembly 114 in order to continue collecting the medical waste in place of the first assembly 114 while the first assembly 114 executes the disposal protocol.

In some embodiments, the controller 28 of the first assembly 114 is configured to provide a replacement signal to the locator network 94 in response to actuation of the user input device 68. The user input device 68 can be actuated by hospital personnel upon filling of the canister 44 of the first assembly 114 during a medical procedure. In response to receiving the replacement signal the locator network 94 provides the first and second location input signals to the controller 28 of the second assembly 116. The controller 28 of the first assembly 114 can initiate the waste disposal procedure and the second assembly 116 can autonomously navigate to the first location to replace the first assembly 114 in receiving the medical waste during the medical procedure. The controller of the second assembly 116 is configured to instruct movement of the second assembly 116 to the first location via the powered wheel of the second assembly 116. The controller of the second assembly 116 instructs movement of the second assembly 116 to the first location to replace the first assembly 114 at the first location.

Figure 10:
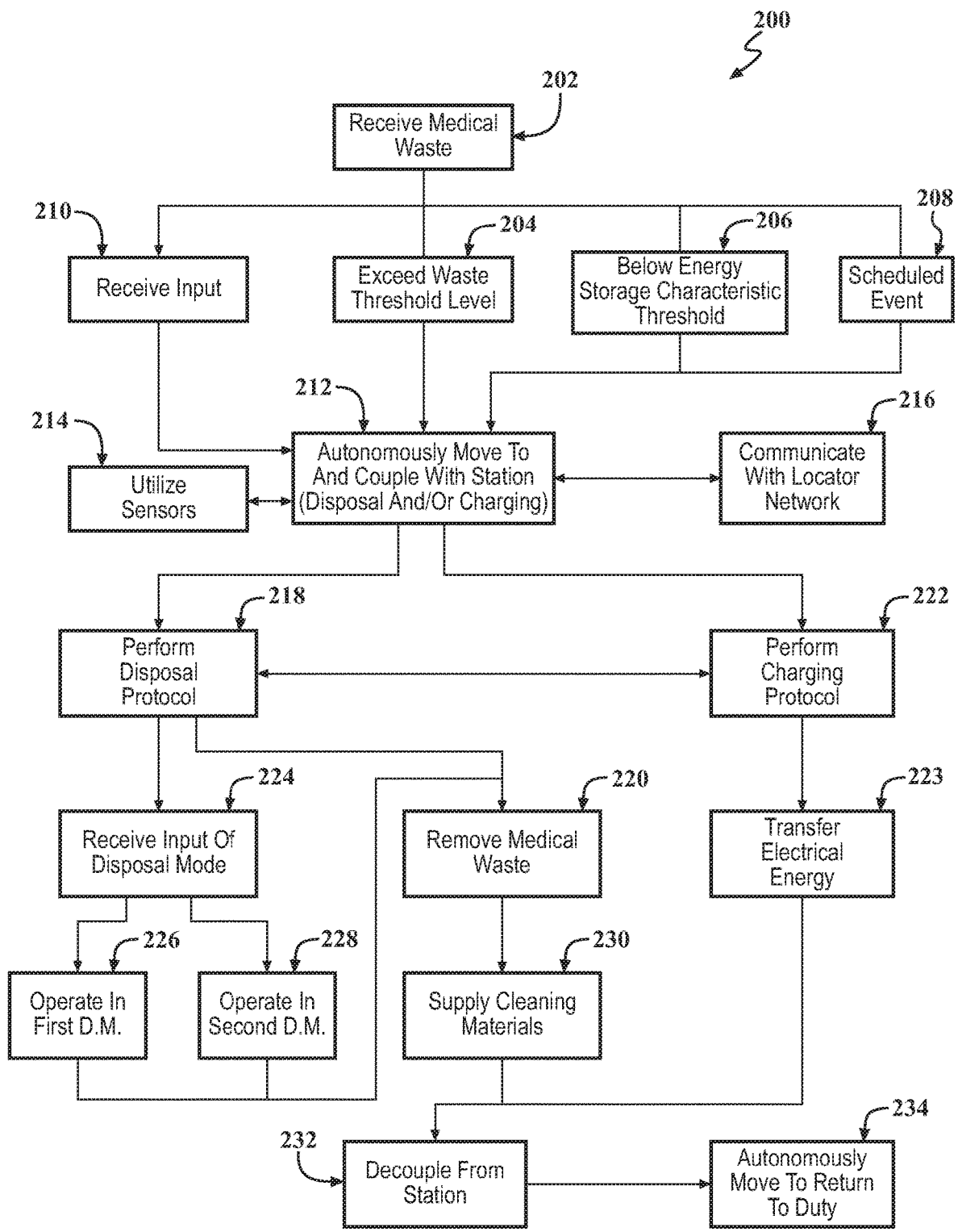
FIG. 10 is a flowchart of an embodiment of a method of operating a medical waste collection system.

Referring to FIG. 10, a method 200 of operating the medical waste collection system 70 is shown. At step 202, the waste collection unit 26 receives the medical waste from a patient during a medical procedure. To do so, the assembly 20 may be positioned near the patient in the medical facility, for example the operating room (see FIG. 7). The user provides an input to the user input device 68 in communication with the controller 28. The controller 28 operates the suction pump 46, and perhaps the vacuum regulator 47, to regulate the level of suction drawn through the suction line 48. The medical waste is stored in at least one of the canisters 44.

In one example, the raw waste level in the canister 44, as detected by the waste sensor 62, exceeds the waste threshold level (step 204). Additionally or alternatively, the energy storage device characteristic of the energy storage device 64, as detected by the energy storage device sensor 66, falls below the energy storage device characteristic threshold (step 206). Additionally or alternatively, a schedule as stored in the memory component 56 may indicate a scheduled performing of the disposal protocol and/or the charging protocol (step 208). Additionally or alternatively, the user may provide an input to the user input device 68. The controller 28 in communication with the user input device 68 receives the input (step 210). For any one or more of the above, the assembly 20 autonomously moves to and couples with the station; i.e., the disposal station 50 (see FIG. 3), the charging station 54 (see FIG. 4), or the integrated disposal-charging station 54 (see FIG. 5) (step 212). For example, at step 212, the controller 28 actuates powered wheel 42 to move the assembly 20 to the disposal station 50. Any one or more of the sensors 82, 112 may be utilized to facilitate the coupling of the assembly 50 with the station 50, 54 (step 214). Further, the locator network 94 of the medical facility in communication with the controller 28 may facilitate navigation of the assembly 20 to the station 50, 54, as previously described (step 216).

At step 218, the assembly 20 performs the disposal protocol while coupled to the disposal station 50. In particular, the disposal station 50 autonomously removes the medical waste from the waste collection unit 26. The disposal station 50 may perform a cleaning operation to clean the canisters 44 (step 230). Should the station be an integrated disposal-charging station 54 (see FIG. 5), the charging station 54 autonomously performs the charging protocol (step 222). In particular, electric power is transferred from the energy source to the energy storage device 64 of the assembly 20 (step 223), which may occur simultaneously with the disposal station 50 autonomously removing the medical waste from the waste collection unit 26. Otherwise, the controller 28 may actuate the powered wheel 42 to move the assembly 20 to the charging station 54. Alternatively, should the energy storage device 64 not need additional electric power, the controller 28 may actuate the powered wheel 42 to move the assembly 20 to return to the duty station or a storage location (step 234). The reversal of steps 218 and 222 are contemplated in which the assembly 20 first couples with the charging station 54. Likewise, should the canister 44 not need emptying subsequent to the energy storage device 64 receiving electric power, the controller 28 may actuate the powered wheel 42 to move the assembly 20 to return to the duty station or a storage location (step 234).

In certain embodiments, the user input device 68 may receive an input from the user as to a disposal mode, for example, a first disposal mode and a second disposal mode. Based on the input from the user, the controller 28 in communication with the user input device 68 may perform the disposal protocol to the medical waste removed for a first amount of time according to the first disposal mode (steps 220 and 226), or for a second amount of time according to the second disposal mode (steps 220 and 228). The second amount of time is different than the first amount of time. The cleaning operation (step 230) may be performed in one or both of the first and second disposal modes.

The assembly 20 may autonomously decouple from the station 50, 54 (step 232). In an aforementioned example, the electromagnet may deenergize, thereby permitting movement of the assembly 20 relative to the station 50, 54. The controller 28 may actuate the powered wheel 42 to move the assembly 20 to return to the duty station or a storage location (step 234).

Clauses for Alternative Protection

Clause I. A method of operating a medical waste collection system including an autonomous waste collection assembly including a base, at least one powered wheel coupled to the base, a controller, a waste level sensor in communication with the controller, an energy storage device sensor in communication with the controller, and waste collection unit coupled to the base, and a disposal station, said method comprising the steps of: receiving with the waste collection unit the medical waste from a patient during a medical procedure; sensing with the waste level sensor a waste level within the waste collection unit; determining with the controller whether the waste level exceeds a waste level threshold; actuating the at least one powered wheel to move the autonomous medical waste collection assembly; navigating with the controller the autonomous medical waste collection assembly to the disposal station; autonomously coupling the autonomous medical waste collection assembly and the disposal station; and performing a disposal protocol to remove with the disposal station the medical waste from the waste collection unit.

Clause II. The method of clause I, wherein the system includes a charging station, said method further comprising the steps of: autonomously coupling the autonomous medical waste collection assembly and the charging station; and transferring electrical energy from an electric source in communication with the charging station to an energy storage device of the autonomous medical waste collection assembly.

Clause III. The method of any one of clauses I and II, further comprising the steps of operating the medical waste collection assembly in a first disposal mode for a first amount of time, and operating the medical waste collection assembly in a second disposal mode for a second amount of time with the first and second amounts of time being different.

Clause IV. The method of clause III, further comprising selecting one of the first disposal mode and the second disposal mode based on at least one of: (i) an amount of the medical waste within the waste collection unit; (ii) an amount of the medical waste to be transferred from the waste collection unit to the canister of the disposal station; (iii) a user input; (iv) a disposal schedule comprising one or more times the waste disposal protocol is to be performed; and (v) and an amount of time the waste collection unit has held the medical waste.

Clause V. The method of any one of clauses I-IV, wherein the autonomous waste collection assembly includes a user input device, said method further comprising the steps of: receiving an input with the user input device to move the autonomous waste collection assembly from an autonomous mode in which the at least one powered wheel is controllable with the controller for autonomous movement, to a manual mode in which the at least one powered wheel is disabled to permit manual movement of the autonomous waste collection assembly.

Clause VI. The method of clause V, wherein the autonomous waste collection assembly includes a clutch mechanism coupled to the at least one powered wheel, wherein disabling the at least one powered wheel includes disengaging the clutch mechanism to permit the at least one powered wheel to rotate freely.

Clause VII. A method of operating a medical waste collection system including an autonomous waste collection assembly comprising a base, at least one powered wheel coupled to the base, a controller, an energy storage device in communication with the controller, a waste collection unit coupled to the base, and a charging station in electrical communication with an electric source, said method comprising the steps of: receiving with the waste collection unit the medical waste from a patient during a medical procedure; sensing with the energy storage device sensor an energy level storage characteristic of the energy storage device; determining with the controller whether the energy level storage characteristic is below an energy level storage characteristic threshold; actuating the at least one powered wheel to move the autonomous medical waste collection assembly; navigating with the controller the autonomous medical waste collection assembly to the charging station; autonomously coupling the autonomous medical waste collection assembly and the charging station; and performing a charging protocol to transfer electrical energy from an electric source of the charging station to an energy storage device of the autonomous medical waste collection assembly.

Clause VIII. A medical waste collection system, said system comprising: a disposal station comprising: a housing; and a coupler coupled to said housing; and an autonomous medical waste collection assembly comprising: a base adapted to be positioned near a patient; wheels coupled to said base with at least one of said wheels being powered to move said base along a floor surface; a waste collection unit coupled to said base for receiving medical waste from the patient including: a canister for holding the medical waste; and a suction pump in fluid communication with said canister and configured to draw a suction on said canister; a counterposing coupler coupled to said base with said counterposing coupler adapted to be removably coupled with said coupler of said disposal station; and a controller operable to initiate a waste disposal protocol, said waste disposal protocol comprising transmitting a movement signal to said powered wheel for automatically moving said autonomous medical waste collection assembly away from the patient to said disposal station such that said coupler couples with said counterposing coupler to provide a connection between said autonomous medical waste collection assembly and said disposal station.

The present invention has been described herein in an illustrative manner. It is to be understood that the terminology which has been used is intended to be in the nature of words of description rather than of limitation. Obviously, many modifications and variations of the invention are possible in light of the above teachings. The invention may be practiced otherwise than as specifically described within the scope of the appended claims.

The invention claimed is:

1. An autonomous medical waste collection assembly, said assembly comprising:
   a base adapted to be positioned near a patient;
   wheels coupled to said base with at least one of said wheels being powered to move said base along a floor surface;
   a waste collection unit coupled to said base for receiving medical waste from the patient including:
      a canister for holding the medical waste; and
      a suction pump in fluid communication with said canister and configured to draw a suction on said canister;
   a controller operable to initiate a waste disposal protocol, said waste disposal protocol comprising transmitting a movement signal to said powered wheel for automatically moving said autonomous medical waste collection assembly away from the patient to a disposal station; and
   a user input device in communication with said controller, said user input device being adapted to provide a user input signal in response to being actuated by a user;
   wherein said controller is configured to initiate said waste disposal protocol in response to receiving said user input signal.

2. The autonomous medical waste collection assembly of claim 1, further comprising a waste sensor in communication with said controller with said waste sensor adapted to sense an amount of the medical waste contained within said canister and provide a waste level signal to said controller, wherein said controller is configured to initiate said waste disposal protocol in response to the amount of the medical waste sensed by said waste sensor exceeding a waste threshold.

3. The autonomous medical waste collection assembly of claim 1, further comprising an energy storage device and an energy storage device sensor in communication with said controller with said energy storage device sensor adapted to sense a characteristic of said energy storage device and provide an energy storage device characteristic signal to said controller, wherein said controller is configured to initiate a charging protocol when said energy storage device characteristic is below an energy storage device characteristic threshold, said charging protocol comprising transmitting a movement signal to said powered wheel for automatically moving said autonomous medical waste collection assembly away from the patient to a charging station.

4. The autonomous medical waste collection assembly of claim 3, wherein said controller is configured to initiate one of said charging protocol and said waste disposal protocol in response to receiving said user input signal.

5. The autonomous medical waste collection assembly of claim 3, further comprising an energy supply device separate from said energy storage device with said energy supply device configured to be arranged in electrical communication with an energy source.

6. The autonomous medical waste collection assembly of claim 1, further comprising memory in communication with said controller and adapted to store a disposal schedule comprising one or more times to initiate said waste disposal protocol with said controller configured to initiate said waste disposal protocol according to said disposal schedule.

7. The autonomous medical waste collection assembly of claim 6, wherein at least one of said one or more times corresponds to an end time of the medical procedure.

8. The autonomous medical waste collection assembly of claim 1, further comprising memory in communication with said controller and adapted to store a charging schedule comprising one or more times to initiate said charging protocol with said controller configured to initiate said charging protocol according to said charging schedule.

9. The autonomous medical waste collection assembly of claim 1, wherein said controller is configured to operate in an autonomous mode in which said controller transmits said movement signal to said powered wheel for automatically moving said autonomous medical waste collection assembly away from the patient to the disposal station, and a manual mode in which controller transmits a disengagement signal to said powered wheel providing for manual movement of said autonomous medical waste collection assembly.

10. The autonomous medical waste collection assembly of claim 9, further comprising a clutch mechanism coupled to said powered wheel and in communication with said controller, wherein said clutch mechanism is configured to operably decouple from said powered wheel in response to said disengagement signal.

11. A medical waste collection system, said system comprising:
   a disposal station comprising:
      a housing; and
      a coupler coupled to said housing; and
   an autonomous medical waste collection assembly comprising:
      a base adapted to be positioned near a patient;
      wheels coupled to said base with at least one of said wheels being powered to move said base along a floor surface;
      a waste collection unit coupled to said base for receiving medical waste from the patient including:
         a canister for holding the medical waste; and
         a suction pump in fluid communication with said canister and configured to draw a suction on said canister;
      a counterposing coupler coupled to said base with said counterposing coupler adapted to be removably coupled with said coupler of said disposal station;
      a controller;

a user input device in communication with said controller, said user input device being adapted to provide a user input signal in response to being actuated by a user; and said controller operable to initiate a waste disposal protocol in response to receiving said user input signal, said waste disposal protocol comprising transmitting a movement signal to said powered wheel for automatically moving said autonomous medical waste collection assembly away from the patient to said disposal station such that said coupler couples with said counterposing coupler to provide a connection between said autonomous medical waste collection assembly and said disposal station.

12. The medical waste collection system of claim 11, wherein said disposal station further comprises a canister adapted to receive the medical waste with said canister of said disposal station being in fluid communication with said waste collection unit of said autonomous medical waste collection assembly when said autonomous medical waste collection assembly is coupled with said disposal station.

13. The medical waste collection system of claim 11, further comprising an energy storage device and an energy storage device sensor in communication with said controller with said energy storage device sensor adapted to sense a characteristic of said energy storage device and provide an energy storage device characteristic signal to said controller, wherein said controller is configured to initiate a charging protocol when said energy storage device characteristic is below an energy storage device characteristic threshold.

14. The medical waste collection system of claim 13, wherein the movement signal is a first movement signal, further comprising a charging station comprising a housing and a coupler coupled to said housing and wherein said charging protocol comprises transmitting a second movement signal to said powered wheel for automatically moving said autonomous medical waste collection assembly away from the patient to said charging station such that said coupler of said charging station couples with said counterposing coupler to provide a connection between said autonomous medical waste collection assembly and said charging station with said charging station in electrical communication with an electric source and adapted to transfer electrical energy from the electric source to said energy storage device when said autonomous medical waste collection assembly is coupled with said charging station.

15. The medical waste collection system of claim 14, wherein said disposal station is in electrical communication with the electric source with said disposal station adapted to transfer electrical energy from the electric source to said energy storage device when said autonomous medical waste collection assembly is coupled with said disposal station.

16. The medical waste collection system of claim 11, wherein said waste disposal protocol comprises a plurality of disposal modes with each of said disposal modes comprising a different amount of time said autonomous waste collection assembly and said disposal station are coupled while removing the medical waste from said waste collection unit.

17. The medical waste collection system of claim 16, wherein said controller is adapted to select one of said disposal modes based on at least one of an amount of the medical waste within said waste collection unit, an amount of the medical waste to be removed from said waste collection unit, and an amount of time the waste collection unit has held the medical waste.

18. The medical waste collection system of claim 16, further comprising memory in communication with said controller and adapted to store a disposal schedule comprising one or more times to initiate said waste disposal protocol with said controller configured to initiate said waste disposal protocol according to said disposal schedule and wherein said controller is adapted to select one of said disposal modes based on a user input or said disposal schedule.

19. The medical waste collection system of claim 11, wherein said controller is configured to receive a current location input signal and a disposal location input signal from a locator network within a medical facility, said current location input signal based on a current location of said autonomous medical waste collection assembly, and said disposal location input signal based on a disposal location of said disposal station, and wherein said controller is configured to navigate said autonomous waste collection assembly to said disposal station based on said current location input signal and said disposal location input signal.

20. The medical waste collection system of claim 19, further comprising memory in communication with said controller and adapted to store a plurality of defined paths within the medical facility with said controller adapted to navigate said autonomous medical waste collection assembly to said disposal station along one of said defined paths based on a distance between the current location of said autonomous medical waste collection assembly and the disposal location of said disposal station.

21. The medical waste collection system of claim 20, further comprising a spatial awareness sensor in communication with said controller and configured to sense objects obstructing said one defined path as said autonomous medical waste collection assembly is navigated between the current location and the disposal location, wherein said controller is adapted to direct said autonomous medical waste collection assembly to deviate from said one defined path in response to said sensed obstruction by said spatial awareness sensor.

* * * * *